(12) United States Patent
Fatheree et al.

(10) Patent No.: US 7,067,482 B2
(45) Date of Patent: Jun. 27, 2006

(54) CROSS-LINKED GLYCOPEPTIDE-CEPHALOSPORIN ANTIBIOTICS

(75) Inventors: Paul R. Fatheree, San Francisco, CA (US); Martin S. Linsell, San Mateo, CA (US); Daniel Marquess, Half Moon Bay, CA (US); Sean G. Trapp, San Francisco, CA (US); Edmund J. Moran, San Francisco, CA (US); James B. Aggen, Burlingame, CA (US)

(73) Assignee: Theravance, Inc., South San Francisco, CA (US)

( * ) Notice: Subject to any disclaimer, the term of this patent is extended or adjusted under 35 U.S.C. 154(b) by 138 days.

(21) Appl. No.: 10/888,849

(22) Filed: Jul. 9, 2004

(65) Prior Publication Data

US 2005/0026818 A1 Feb. 3, 2005

Related U.S. Application Data

(60) Provisional application No. 60/486,484, filed on Jul. 11, 2003.

(51) Int. Cl.
*A61K 38/16* (2006.01)
(52) U.S. Cl. ............... 514/8; 530/322; 530/317; 530/320; 514/9; 514/23
(58) Field of Classification Search ............... None
See application file for complete search history.

(56) References Cited

U.S. PATENT DOCUMENTS 4,220,761 A 9/1980 Takaya et al.
4,341,775 A 7/1982 Takaya et al.
4,366,153 A 12/1982 Takaya et al.
4,487,767 A 12/1984 Takaya et al.
4,921,851 A 5/1990 Kishimoto et al.
4,943,567 A 7/1990 Nishizawa et al.
5,693,791 A 12/1997 Truett et al.
6,437,119 B1 8/2002 Truett
6,878,686 B1* 4/2005 Marquess et al. ............ 514/8
2003/0130173 A1 7/2003 Fatheree et al.
2004/0033939 A1 2/2004 Marquess et al.
2004/0266666 A1 12/2004 Fatheree et al.
2005/0005436 A1* 1/2005 Chang ..................... 29/841
2005/0209132 A1* 9/2005 Marquess et al. ............ 514/8

FOREIGN PATENT DOCUMENTS

| GB | 2 033 377 A | 5/1980 |
|---|---|---|
| WO | WO 99/42476 A1 | 8/1999 |
| WO | WO 99/64049 A1 | 12/1999 |
| WO | WO 00/39156 A1 | 7/2000 |
| WO | WO 03/031449 A3 | 4/2003 |
| WO | WO 03/099858 A1 | 12/2003 |

OTHER PUBLICATIONS

U.S. Appl. No. 09/457,926, filed Dec. 8, 1999, Christensen et al.

(Continued)

*Primary Examiner*—Bruce R. Campell
*Assistant Examiner*—Andrew D. Kosar
(74) *Attorney, Agent, or Firm*—Jeffrey A. Hagenah

(57) ABSTRACT

This invention provides cross-linked glycopeptide—cephalosporin compounds and pharmaceutically acceptable salts thereof which are useful as antibiotics. This invention also provides pharmaceutical compositions containing such compounds; methods for treating bacterial infections in a mammal using such compounds; and processes and intermediates useful for preparing such compounds.

28 Claims, 3 Drawing Sheets

OTHER PUBLICATIONS

Boeckh et al., "Pharmacokinetics and Serum Bactericidal Activity of Vancomycin Alone and in Combination with Ceftazidime in Healthy Volunteers", Antibacterial Agents and Chemotherapy, vol. 32, No. 1, pp. 92-95 (1988).

Hammes, W. P., "Biosynthesis of Peptidoglycan in *Gaffkya homari*. The Mode of Action of Penicillin G and Mecillinam", Eur. J. Biochem., vol. 70, pp. 107-113 (1976).

Kim et al., "Synthesis and Antibacterial Activity of Cephalosporins Having Hydroxamic Acid at C-7 Position", Biorganic & Med. Chem. Letters, vol. 6, No. 17, pp. 2077-2080 (1996).

Lattrell et al., "Synthesis and Structure-Activity Relationships in the Cefpirome Series", Journal of Antibiotics, vol. XLI, No. 10, pp. 1374-1394 (1988).

Pavlov et al., A New Type of Chemical Modification of Glycopeptides Antibiotics: Aminomethylated Derivatives of Eromomycin and Their Antibacterial Activity, The Journal of Antibiotics, vol. 50, No. 6, pp. 509-513 (1997).

Pavlov et al., "Chemical Modification of Glycopeptide Antibiotics [VC1]", Russian Journal of Bioorganiz Chemistry, vol. 24, No. 9, pp. 570-587 (1998).

Rao et al., "Tight Binding of a Dimeric Derivative of Vancomycin with Dimeric L-Lys-D-Ala-D-Ala", J. Am. Chem. Soc., vol. 119, pp. 10286-10290 (1997).

Renoud-Grappin et al., "Imidazo[1,5-b]pyridazine-d4T conjugates:synthesis and anti-human immunodeficiency virus evaluation", Antiviral Chemistry & Chemotherapy, vol. 9, pp. 205-223.

Staroske et al., "Synthesis of Covalent Head-to-Tail Dimers of Vancomycin", Tetrahedron Letters, vol. 39, pp. 4917-4920 (1998).

Sundram et al., "General and Efficient Method for the Solution-and Solid-Phase Synthesis of Vancomycin Carboxamide Derivatives", J. Org. Chem., vol. 60, pp. 1102-1103 (1995).

Sundram et al., "Novel Vancomycin Dimers with Activity against Vancoymcin-Resistant Enterococci", J. Am. Chem. Soc., vol. 118, pp. 13107-13108 (1996).

\* cited by examiner

CROSS-LINKED GLYCOPEPTIDE-CEPHALOSPORIN ANTIBIOTICS

CROSS-REFERENCE TO RELATED APPLICATIONS

This application claims the benefit of U.S. Provisional Application No. 60/486,484, filed on Jul. 11, 2003; the entire disclosure of which is incorporated herein by reference in its entirety.

BACKGROUND OF THE INVENTION

1. Field of the Invention

This invention is directed to novel cross-linked vancomycin—cephalosporin compounds which are useful as antibiotics. This invention is also directed to pharmaceutical compositions comprising such compounds; methods of using such compounds as antibacterial agents; and processes and intermediates for preparing such compounds.

2. State of the Art

Various classes of antibiotic compounds are known in the art including, for example, β-lactam antibiotics, such as cephalosporins, and glycopeptide antibiotics, such as vancomycin. Cross-linked antibiotic compounds are also known in the art. See, for example, U.S. Pat. No. 5,693,791, issued to W. L. Truett and entitled "Antibiotics and Process for Preparation"; and WO 99/64049 A1, published on Dec. 16, 1999, and entitled "Novel Antibacterial Agents." Additionally, WO 03/031449 A2, published on Apr. 17, 2003, and entitled "Cross-Linked Glycopeptide—Cephalosporin Antibiotics" discloses compounds having a glycopeptide group covalently linked to the oxime moiety of a cephalosporin group.

Due to the potential for bacteria to develop resistance to antibiotics, however, a need exists for new antibiotics having unique chemical structures. Additionally, a need exists for novel antibiotics having improved antibacterial properties including, by way of example, increased potency against Gram-positive bacteria. In particular, a need exists for new antibiotics that are highly effective against antibiotic-resistant strains of bacteria, such as methicillin-resistant *Staphylococci aureus* (MRSA).

SUMMARY OF THE INVENTION

The present invention provides novel cross-linked glycopeptide—cephalosporin compounds that are useful as antibiotics. The compounds of this invention have a unique chemical structure in which a glycopeptide group is covalently linked to a pyridinium moiety of a cephalosporin group. Among other properties, compounds of this invention have been found to possess surprising and unexpected potency against Gram-positive bacteria including methicillin-resistant *Staphylococci aureus* (MRSA).

Accordingly, in one aspect, the invention provides a compound of formula I:

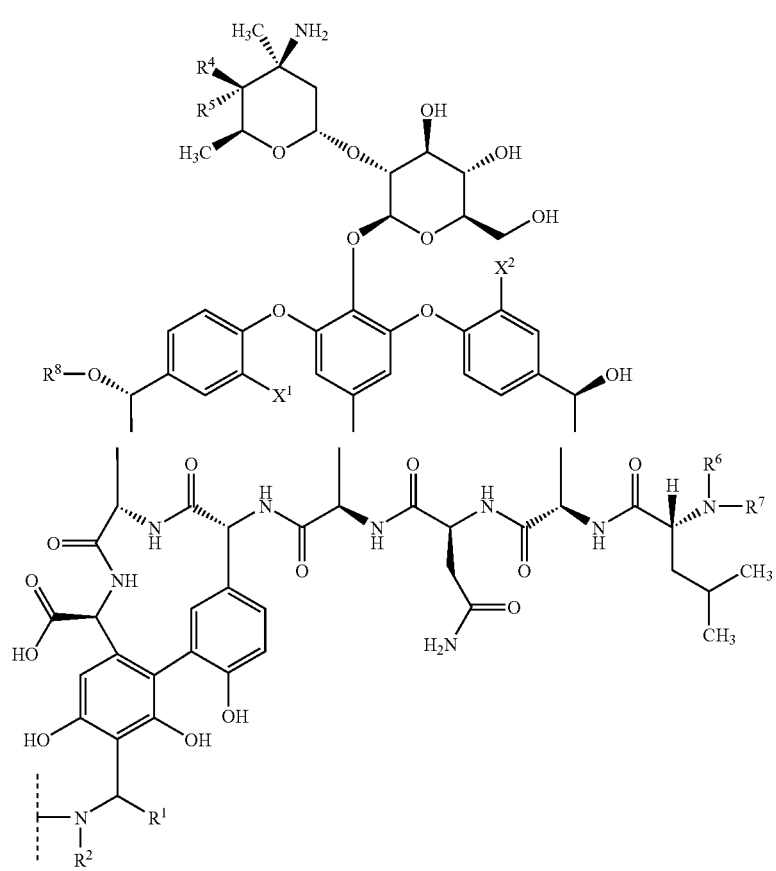

-continued

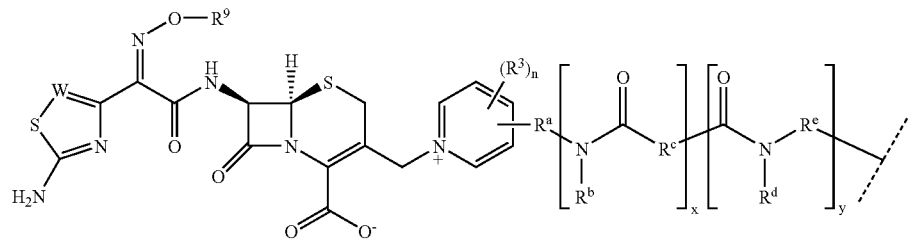

or a pharmaceutically-acceptable salt thereof; wherein
each of $X^1$ and $X^2$ is independently hydrogen or chloro;
W is N or CCl;
$R^1$ and $R^2$ are independently selected hydrogen and $C_{1-6}$ alkyl;
each $R^3$ is independently selected from $C_{1-6}$ alkyl, OR, halo, —SR, —S(O)R, —S(O)$_2$R, and —S(O)$_2$OR, where each R is independently $C_{1-6}$ alkyl optionally substituted with COOH or 1 to 3 fluoro substituents;
one of $R^4$ and $R^5$ is hydroxy and the other is hydrogen;
$R^6$ and $R^7$ are independently hydrogen or methyl;
$R^8$ is hydrogen or a group of the formula:

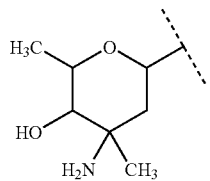

$R^9$ is selected from hydrogen, $C_{1-6}$ alkyl and $C_{3-6}$ cycloalkyl, where alkyl and cycloalkyl are optionally substituted with —COOH or 1 to 3 fluoro substituents;
$R^a$ is —Y—R"—, where R" is selected from $C_{1-12}$ alkylene, $C_{2-12}$ alkenylene, $C_{2-12}$ alkynylene, $C_{3-6}$ cycloalkylene, $C_{6-10}$ arylene, $C_{2-9}$ heteroarylene, $C_{3-6}$ heterocycle and combinations thereof, and is optionally substituted with 1 or 2 groups selected from Z, where each Z is independently selected from —OR', —SR', —F, —Cl, —N(R')$_2$, —OC(O)R', —C(O)OR', —NHC(O)R', —C(O)N(R')$_2$, —CF$_3$, —OCF$_3$, and side chains of naturally-occurring amino acids, where each R' is independently hydrogen or $C_{1-4}$ alkyl; and R" contains at most 20 non-hydrogen atoms; and Y, which links R" to the pyridinium ring at a meta or para position, is selected from the group consisting of a direct bond, NR', O (ether), S (sulfide), C(O) (carbonyl), NR'C(O), and C(O)NR', precluding direct bonds between heteroatoms in Y and R";
each $R^b$ and $R^d$ is independently selected from hydrogen, $C_{1-6}$ alkyl, $C_{2-6}$ alkenyl and $C_{2-6}$ alkynyl;
each $R^c$ is independently a direct bond or —Y'—R"—Y'—, where each Y' is independently selected from a direct bond, O (ether) and NR', precluding direct bonds between heteroatoms in Y' and R";
each $R^e$ is independently selected from the group defined by R" above;
n is an integer from 0 to 3;
x is an integer from 0 to 2; and
y is an integer from 0 to 2.

In another of its composition aspects, this invention provides a compound of formula

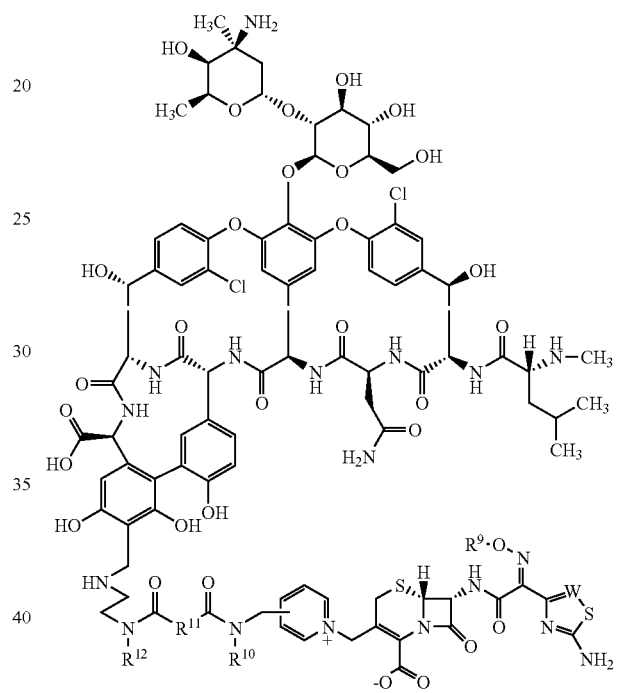

or a pharmaceutically acceptable salt thereof; wherein
W is N or CCl;
$R^9$ is selected from hydrogen, $C_{1-6}$ alkyl and $C_{3-6}$ cycloalkyl, where alkyl and cycloalkyl are optionally substituted with —COOH or 1 to 3 fluoro substituents;
the pyridinium ring has meta or para substitution;
$R^{10}$ is hydrogen, $C_{1-4}$ alkyl or $C_{2-4}$ alkenyl;
$R^{11}$ is $C_{1-12}$ alkylene or $C_{2-12}$ alkenylene; and
$R^{12}$ is hydrogen, $C_{1-4}$ alkyl or $C_{2-4}$ alkenyl.

In another of its composition aspects, this invention provides a pharmaceutical composition comprising a pharmaceutically-acceptable carrier and a therapeutically effective amount of a compound of formula I, or a pharmaceutically-acceptable salt thereof; including any of the particular embodiments discussed herein.

The compounds of this invention are useful as antibacterial agents. Accordingly, in one of its method aspects, this invention provides a method of treating a bacterial infection in a mammal, the method comprising administering to a mammal a pharmaceutical composition comprising a pharmaceutically-acceptable carrier and a therapeutically effective amount of a compound of formula I, or a pharmaceutically-acceptable salt thereof; including any of the particular embodiments discussed herein.

While not intending to be limited by theory, the compounds of this invention are believed to inhibit bacterial cell wall biosynthesis thereby inhibiting the growth of the bacteria or causing lysis of the bacteria. Accordingly, in another of its method aspects, this invention provides a method of inhibiting the growth of bacteria, the method comprising contacting bacteria with a growth-inhibiting amount of a compound of formula I, or a pharmaceutically-acceptable salt thereof, including any of the particular embodiments discussed herein.

Additionally, in yet another of its method aspects, this invention provides a method of inhibiting bacterial cell wall biosynthesis, the method comprising contacting bacteria with a cell wall biosynthesis-inhibiting amount of a compound of formula I, or a pharmaceutically-acceptable salt thereof, including any of the particular embodiments discussed herein.

This invention is also directed to processes for preparing compounds of formula I or a salt thereof. Accordingly, in another of its method aspects, this invention provides a process for preparing a compound of formula I, or a salt thereof; the process comprising reacting a compound of formula 1 or a salt, activated derivative, or protected derivative thereof, with a compound of formula 2 or a salt, activated derivative, or protected derivative thereof; and a compound of formula 3 or a salt, activated derivative, or protected derivative thereof, to form the compound of formula I, wherein the compounds of formula 1, 2 and 3 are as defined herein.

In one embodiment, the above process further comprise the step of forming a pharmaceutically-acceptable salt of a compound of formula I. This invention is also directed to the product prepared by any of these processes described herein.

This invention is also directed to a compound of formula I, or a pharmaceutically acceptable salt thereof, for use in therapy. Additionally, this invention is directed to the use of a compound of formula I, or a pharmaceutically-acceptable salt thereof, for the manufacture of a medicament, including a medicament for treating a bacterial infection in a mammal.

DETAILED DESCRIPTION OF THE INVENTION

Figure 1:
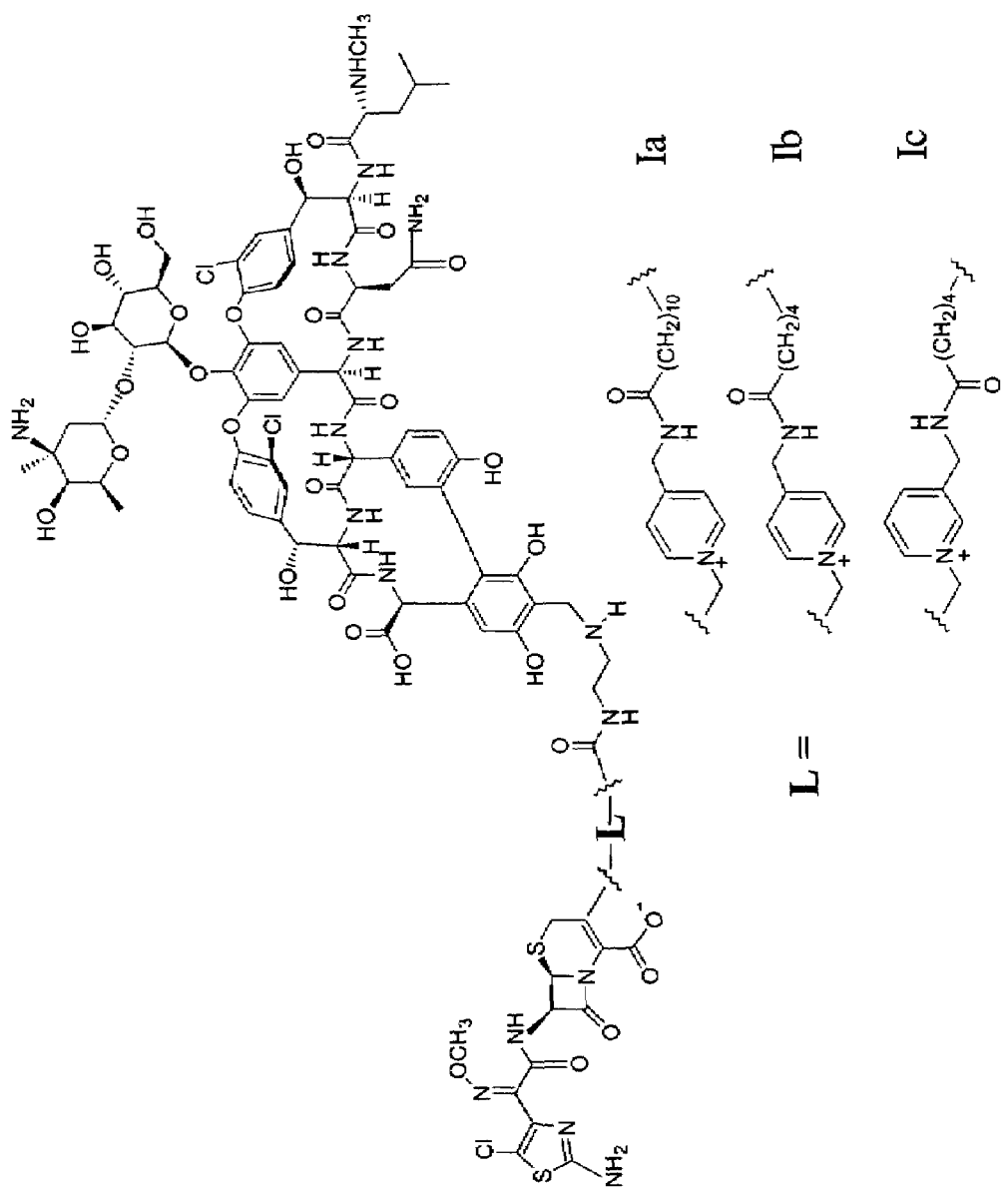
FIG. 1 shows representative examples of cross-linked glycopeptide—cephalosporin antibiotics in accordance with selected embodiments of the invention.

This invention provides novel glycopeptide—cephalosporin compounds of formula I, or pharmaceutically acceptable salts thereof. These compounds have multiple chiral centers and, in this regard, the compounds are intended to have the stereochemistry shown. In particular, the glycopeptide portion of the compound is intended to have the stereochemistry of the corresponding naturally-occurring glycopeptide (i.e., vancomycin, chloroorienticin A and the like). The cephalosporin portion of the molecule is intended to have the stereochemistry of known cephalosporin compounds. However, it will be understood by those skilled in the art that minor amounts of isomers having a different stereochemistry from that shown may be present in the compositions of this invention provided that the utility of the composition as a whole is not precluded by the presence of such isomers.

Additionally, the linking portion of the compounds of this invention may contain one or more chiral centers. Typically, this portion of the molecule will be prepared as a racemic mixture. If desired, however, pure stereoisomers (i.e., individual enantiomers or diastereomers) may be used or a stereoisomer-enriched mixture can be employed. All such stereoisomers and enriched mixtures are included within the scope of this invention.

In addition, compounds of this invention contain several acidic groups (i.e., carboxylic acid groups) and several basic groups (i.e., primary and secondary amine groups) and therefore, the compounds of formula I can exist in various salt forms. All such salt forms are included within the scope of this invention. Also, since the compounds of formula I contain a pyridinium ring, an anionic counterion for the pyridinium group may optionally be present including, but not limited to, halides, such as chloride; carboxylates, such as acetate; and the like.

DEFINITIONS

The following terms, as used herein, have the following meanings, unless otherwise indicated:

The term "alkyl" means a monovalent saturated hydrocarbon group which may be linear or branched. Unless otherwise defined, such alkyl groups typically contain from 1 to 10 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkylene" means a divalent saturated hydrocarbon group which may be linear or branched. Unless otherwise defined, such alkylene groups typically contain from 1 to 10 carbon atoms. Representative alkylene groups include, by way of example, methylene, ethane-1,2-diyl ("ethylene"), propane-1,2-diyl, propane-1,3-diyl, butane-1,4-diyl, pentane-1,5-diyl and the like.

The term "alkenyl" means a monovalent unsaturated hydrocarbon group which may be linear or branched and which has at least one, and typically 1, 2 or 3, carbon-carbon double bonds. Unless otherwise defined, such alkenyl groups typically contain from 2 to 10 carbon atoms. Representative alkenyl groups include, by way of example, ethenyl, n-propenyl, isopropenyl, n-but-2-enyl, n-hex-3-enyl and the like.

The term "alkynyl" means a monovalent unsaturated hydrocarbon group which may be linear or branched and which has at least one, and typically 1, 2 or 3, carbon-carbon triple bonds. Unless otherwise defined, such alkynyl groups typically contain from 2 to 10 carbon atoms. Representative alkynyl groups include, by way of example, ethynyl, n-propynyl, n-but-2-ynyl, n-hex-3-ynyl and the like.

The term "aryl" means a monovalent aromatic hydrocarbon having a single ring (i.e., phenyl) or fused rings (i.e., naphthalene). Unless otherwise defined, such aryl groups typically contain from 6 to 10 carbon ring atoms. Representative aryl groups include, by way of example, phenyl and naphthalene-1-yl, naphthalene-2-yl, and the like.

The term "arylene" means a divalent aromatic hydrocarbon having a single ring (i.e., phenylene) or fused rings (i.e., naphthalenediyl). Unless otherwise defined, such arylene groups typically contain from 6 to 10 carbon ring atoms. Representative arylene groups include, by way of example, 1,2-phenylene, 1,3-phenylene, 1,4-phenylene, naphthalene-1,5-diyl, naphthalene-2,7-diyl, and the like.

The term "cycloalkyl" means a monovalent saturated carbocyclic hydrocarbon group. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl and the like.

The term "cycloalkylene" means a divalent saturated carbocyclic hydrocarbon group. Unless otherwise defined, such cycloalkylene groups typically contain from 3 to 10 carbon atoms. Representative cycloalkylene groups include, by way of example, cyclopropane-1,2-diyl, cyclobutyl-1,2-diyl, cyclobutyl-1,3-diyl, cyclopentyl-1,2-diyl, cyclopentyl-1,3-diyl, cyclohexyl-1,2-diyl, cyclohexyl-1,3-diyl, cyclohexyl-1,4-diyl, and the like.

The term "halo" means fluoro, chloro, bromo and iodo.

The term "heteroaryl" means a monovalent aromatic group having a single ring or two fused rings and containing in the ring at least one heteroatom (typically 1 to 3 heteroatoms) selected from nitrogen, oxygen or sulfur. Unless otherwise defined, such heteroaryl groups typically contain from 5 to 10 total ring atoms. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom.

The term "heteroarylene" means a divalent aromatic group having a single ring or two fused rings and containing at least one heteroatom (typically 1 to 3 heteroatoms) selected from nitrogen, oxygen or sulfur in the ring. Unless otherwise defined, such heteroarylene groups typically contain from 5 to 10 total ring atoms. Representative heteroarylene groups include, by way of example, divalent species of pyrrole, imidazole, thiazole, oxazole, furan thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom.

The term "heterocyclyl" or "heterocyclic" means a monovalent or divalent saturated or unsaturated (non-aromatic) group having a single ring or multiple condensed rings and containing in the ring at least one heteroatom (typically 1 to 3 heteroatoms) selected from nitrogen, oxygen or sulfur. Unless otherwise defined, such heterocyclic groups typically contain from 2 to 9 total ring atoms. Representative heterocyclic groups include, by way of example, monovalent species of pyrrolidine, imidazolidine, pyrazolidine, piperidine, 1,4-dioxane, morpholine, thiomorpholine, piperazine, 3-pyrroline and the like, where the point of attachment is at any available carbon or nitrogen ring atom.

The term "cephalosporin" is used herein in its art-recognized manner to refer to a β-lactam ring system having the following general formula and numbering system:

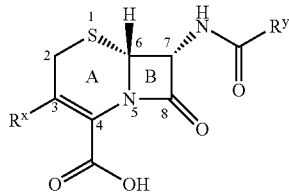

where $R^x$ and $R^y$ represent the remaining portion of the cephalosporin.

The term "glycopeptide antibiotic" or "glycopeptide" is used herein in its art-recognized manner to refer to the class of antibiotics known as glycopeptides or dalbahpeptides. See, for example, R. Nagarajan, "Glycopeptide Antibiotics", Marcel Dekker, Inc. (1994) and references cited therein. Representative glycopeptides include vancomycin, A82846A (eremomycin), A82846B (chloroorienticin A), A82846C, PA-42867-A (orienticin A), PA-42867-C, PA-42867-D and the like.

The term "vancomycin" is used herein in its art-recognized manner to refer to the glycopeptide antibiotic known as vancomycin. When vancomycin is employed in the compounds of the present invention, the point of attachment for the linking moiety is amino acid 7 (AA-&) at position C-29. This position is also sometimes referred to as the "7d" or the "resorcinol" position of vancomycin.

The term "cross-linked glycopeptide—cephalosporin antibiotics" means covalent conjugation of a glycopeptide component to a cephalosporin component.

The term "pharmaceutically-acceptable salt" means a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids. Salts derived from pharmaceutically-acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically-acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like. Particularly preferred are citric, hydrobromic, hydrochloric, maleic, phosphoric, sulfuric and tartaric acids.

The term "salt thereof" means a compound formed when the hydrogen of an acid is replaced by a cation, such as a metal cation or an organic cation and the like (e.g., an $NH_4^+$ cation and the like). Preferably, the salt is a pharmaceutically-acceptable salt, although this is not required for salts of intermediate compounds which are not intended for administration to a patient.

The term "therapeutically effective amount" means an amount sufficient to effect treatment when administered to a patient in need of treatment.

The term "treating" or "treatment" as used herein means the treating or treatment of a disease or medical condition (such as a bacterial infection) in a patient, such as a mammal (particularly a human or a companion animal) which includes:

(a) preventing the disease or medical condition from occurring, i.e., prophylactic treatment of a patient;

(b) ameliorating the disease or medical condition, i.e., eliminating or causing regression of the disease or medical condition in a patient;

(c) suppressing the disease or medical condition, i.e., slowing or arresting the development of the disease or medical condition in a patient; or (d) alleviating the symptoms of the disease or medical condition in a patient.

The term "growth-inhibiting amount" means an amount sufficient to inhibit the growth or reproduction of a microorganism or sufficient to cause death or lysis of the microorganism including Gram-positive bacteria.

The term "cell wall biosynthesis-inhibiting amount" means an amount sufficient to inhibit cell wall biosynthesis in a microorganism including Gram-positive bacteria.

The term "leaving group" means a functional group or atom which can be displaced by another functional group or atom in a substitution reaction, such as a nucleophilic substitution reaction. By way of example, representative leaving groups include chloro, bromo and iodo groups; and sulfonic ester groups, such as mesylate, tosylate, brosylate, nosylate and the like; activated ester groups, such as such as 7-azabenzotriazole-1-oxy and the like; acyloxy groups, such as acetoxy, trifluoroacetoxy and the like.

The term "protected derivatives thereof" means a derivative of the specified compound in which one or more functional groups of the compound are protected from undesired reactions with a protecting or blocking group. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, N.Y., 1999, and references cited therein.

The term "amino-protecting group" means a protecting group suitable for preventing undesired reactions at an amino group. Representative amino-protecting groups include, but are not limited to, tert-butoxycarbonyl (BOC), trityl (Tr), benzyloxycarbonyl (Cbz), 9-fluorenylmethoxycarbonyl (Fmoc), formyl, trimethylsilyl (TMS), tert-butyldimethylsilyl (TBS), and the like.

The term "carboxy-protecting group" means a protecting group suitable for preventing undesired reactions at a carboxy group (i.e., —COOH). Representative carboxy-protecting groups include, but are not limited to, esters, such as methyl, ethyl, tert-butyl, benzyl (Bn), p-methoxybenzyl (PMB), 9-fluorenylmethyl (Fm), trimethylsilyl (TMS), tert-butyldimethylsilyl (TBS), diphenylmethyl (benzhydryl, DPM) and the like.

An "activated derivative", with respect to a carboxylic acid or protected derivative thereof, or such an acid or derivative in "activated form", means the product, typically a reactive ester, resulting from reaction of the carboxylic acid or derivative with an activating (coupling) agent, such as, for example, 1-hydroxybenzotriazole (HOBT), 1-hydroxy-7-azabenzotriazole (HOAT), or others described herein or otherwise known in the art.

A "side chain of a naturally occurring amino acid" means the group R in the formula $HOOC-CHR-NH_2$, where this formula represents an amino acid selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine; including the group selected from alanine, arginine, asparagine, aspartic acid, cysteine, glutamine, glutamic acid, glycine, isoleucine, leucine, lysine, methionine, serine, threonine and valine.

REPRESENTATIVE EMBODIMENTS

The following substituents and values are intended to provide representative examples and embodiments of various aspects of this invention. These representative values are intended to further define such aspects and embodiments and are not intended to exclude other embodiments or limit the scope of this invention. In this regard, the representation that a particular value or substituent is preferred is not intended in any way to exclude other values or substituents from this invention unless specifically indicated.

In compounds of formula I, each heteroaryl or heterocyclic group, when present in R", preferably has 5 or 6 total ring atoms; and each aryl group, when present, preferably has 6 total ring atoms. The group R" is preferably $C_{1-12}$ alkylene, and is preferably linear.

In a specific embodiment, $R^1$ is hydrogen or $C_{1-4}$ alkyl, such as methyl or ethyl. In another embodiment, $R^1$ is hydrogen.

In another specific embodiment, $R^2$ is hydrogen or $C_{1-4}$ alkyl, such as methyl or ethyl. In another embodiment, $R^2$ is hydrogen.

Each $R^3$ group, when present, is preferably independently selected from $C_{1-4}$ alkyl, $C_{1-4}$ alkoxy, fluoro, and chloro. In one embodiment, n is 1 or 2, and each $R^3$ is independently selected from methyl, methoxy, fluoro, and chloro. In another embodiment, n is zero, such that no $R^3$ group is present.

The pyridinium ring in formula I is typically meta or para substituted, more generally para substituted.

In one embodiment, $R^8$ is hydrogen. In another embodiment, $R^8$ is a group of the formula:

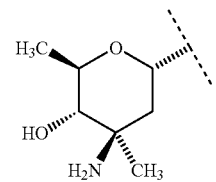

In a specific embodiment, $R^9$ is hydrogen, $C_{1-4}$ alkyl and $C_{3-5}$ cycloalkyl, where the alkyl group is optionally substituted with —COOH or 1 to 3 fluoro substituents; including hydrogen, methyl, ethyl, 2-fluoroethyl, 2-carboxyprop-2-yl and cyclopentyl.

In one embodiment, W is CCl. In another embodiment, W is N.

Specific embodiments of other variables of formula I include, independent of each other, where $X^1$ and $X^2$ are both chloro; where $R^4$ and $R^5$ are OH and hydrogen, respectively; where $R^6$ and $R^7$ are hydrogen and methyl, respectively.

In one embodiment, $R^a$ is —Y—R"—, where R" is $C_{1-6}$ alkylene, $C_{2-6}$ alkenylene or $C_{2-6}$ alkynylene, and Y is selected from a direct bond, NR', ether, sulfide, carbonyl, NR'C(O), and C(O)NR', where R' is hydrogen or methyl. In specific embodiments, in the group $R^a$, Y is a direct bond, and R" is $C_{1-6}$ alkylene, including $C_{1-4}$ alkylene, e.g. methylene.

In specific embodiments, x and y are independently selected from 0 and 1. Accordingly, specific embodiments include compounds in which x+y=0, compounds in which x+y=1 (i.e., x is 1 and y is 0; or x is 0 and y is 1), and compounds in which x+y=2. Additionally, specific embodiments include compounds in which the "linker" structure, represented by —$R^a$—[$NR^b$—C(O)—$R^c$]$_x$—[C(O)—$NR^d$—$R^e$]$_y$—$NR^2$— in formula I, is no more than about 40 atoms in length, and preferably no more than about 30 atoms in length (measured using the shortest number of consecutive atoms in the linker).

In selected embodiments, where x is not 0, and is preferably 1, the $R^b$ is hydrogen, $C_{1-4}$ alkyl or $C_{2-4}$ alkenyl.

In one embodiment, $R^c$ is —Y'—R"—Y'—, where each Y' is independently selected from a direct bond, O (ether), and NR', where R' is hydrogen or methyl, and R" is selected from the group consisting of $C_{1-12}$ alkylene, $C_{2-12}$ alkenylene and $C_{2-12}$ alkynylene. Preferably, in the group $R^c$, Y' is a direct bond, and R" is $C_{1-12}$ alkylene. More preferably, in the group $R^c$, R" is $C_{2-6}$ alkylene.

In other selected embodiments, where y is not 0, and is preferably 1, the variable $R^d$ is hydrogen, $C_{1-4}$ alkyl or $C_{2-4}$ alkenyl, preferably hydrogen or methyl, and more preferably hydrogen.

In one embodiment, $R^b$ and $R^d$ are independently hydrogen or methyl.

In one embodiment, $R^e$ is selected from $C_{1-12}$ alkylene, $C_{2-12}$ alkenylene and $C_{2-12}$ alkynylene; preferably, from $C_{1-6}$ alkylene, $C_{2-6}$ alkenylene and $C_{2-6}$ alkynylene; and more preferably, from $C_{1-4}$ alkylene.

One exemplary class of compounds of formula I is that in which: x is 0 or 1; y is 0 or 1; $R^a$ is methylene; $R^b$ (when x is 1) is hydrogen, methyl, or ethyl; $R^c$ (when x is 1) is $C_{2-12}$ alkylene, e.g. n-butylene (—$(CH_2)_4$—) or n-decylene (—$(CH_2)_{10}$—), which may be substituted with —COOH; $R^d$ (when y is 1) is hydrogen; and $R^e$ (when y is 1) is ethylene (—$CH_2CH_2$—).

In one embodiment, the compounds of this invention are those of formula II. In formula II, a specific embodiment for W is CCl.

Specific embodiments for $R^9$ are hydrogen, $C_{1-4}$ alkyl and $C_{3-5}$ cycloalkyl, where the alkyl group is optionally substituted with —COOH or 1 to 3 fluoro substituents; including hydrogen, methyl, ethyl, 2-fluoroethyl, 2-carboxyprop-2-yl and cyclopentyl.

Specific embodiments for $R^{10}$ are hydrogen or methyl.

A specific embodiment for $R^{11}$ is $C_{1-10}$ alkylene, including $C_{1-6}$ alkylene; such as —$CH_2$—, —$(CH_2)_2$—, —$(CH_2)_3$—, —$(CH_2)_4$—, —$(CH_2)_5$—and —$(CH_2)_6$—.

Specific embodiments for $R^{12}$ are hydrogen, $C_{1-4}$ alkyl or $C_{2-4}$ alkenyl; including hydrogen or methyl.

A specfic embodiment of a compound of formula II, is a compound wherein W is CCl; $R^9$ is methyl; $R^{10}$ is hydrogen; $R^{11}$ is —$(CH_2)_4$—; $R^{12}$ is hydrogen; and the pyridinium ring is para substituted.

As for formula I above, the pyridinium ring in formula II is typically meta or para substituted, more generally para substituted.

Specific embodiments of compounds of this invention include compounds of formula II, or pharmaceutically acceptable salts thereof, wherein the substituents are as defined in Table I:

TABLE I

| Cmpd. No. | $R^9$ | $R^{10}$ | $R^{11}$ | $R^{12}$ | W | Pyridinium Substitution |
|---|---|---|---|---|---|---|
| Ia | —$CH_3$ | —H | —$(CH_2)_{10}$— | —H | CCl | para |
| Ib | —$CH_3$ | —H | —$(CH_2)_4$— | —H | CCl | para |
| Ic | —$CH_3$ | —H | —$(CH_2)_4$— | —H | CCl | meta |
| Id | —$CH_3$ | —H | —$CH_2$— | —H | CCl | para |
| Ie | —$CH_3$ | —H | —$CH_2$— | —H | CCl | meta |
| If | —$CH_3$ | —H | —$(CH_2)_2$— | —H | CCl | para |
| Ig | —$CH_3$ | —H | —$(CH_2)_2$— | —H | CCl | meta |
| Ih | —$CH_3$ | —H | —$(CH_2)_3$— | —H | CCl | para |
| Ii | —$CH_3$ | —H | —$(CH_2)_3$— | —H | CCl | meta |
| Ij | —$CH_3$ | —H | —$(CH_2)_5$— | —H | CCl | para |
| Ik | —$CH_3$ | —H | —$(CH_2)_5$— | —H | CCl | meta |
| Il | —$CH_3$ | —H | —$(CH_2)_6$— | —H | CCl | para |
| Im | —$CH_3$ | —H | —$(CH_2)_6$— | —H | CCl | meta |
| In | —$CH_3$ | —H | —$(CH_2)_7$— | —H | CCl | para |
| Io | —$CH_3$ | —H | —$(CH_2)_7$— | —H | CCl | meta |
| Ip | —$CH_3$ | —H | —$(CH_2)_8$— | —H | CCl | para |
| Iq | —$CH_3$ | —H | —$(CH_2)_8$— | —H | CCl | meta |
| Ir | —$CH_3$ | —H | —$(CH_2)_9$— | —H | CCl | para |
| Is | —$CH_3$ | —H | —$(CH_2)_9$— | —H | CCl | meta |
| It | —$CH_3$ | —H | —$(CH_2)_{10}$— | —H | CCl | meta |
| Iu | —$CH_3$ | —H | —$(CH_2)_{11}$— | —H | CCl | para |

TABLE I-continued

| Cmpd. No. | $R^9$ | $R^{10}$ | $R^{11}$ | $R^{12}$ | W | Pyridinium Substitution |
|---|---|---|---|---|---|---|
| Iv | —$CH_3$ | —H | —$(CH_2)_{11}$— | —H | CCl | meta |
| Iw | —$CH_3$ | —H | —$(CH_2)_{12}$— | —H | CCl | para |
| Ix | —$CH_3$ | —H | —$(CH_2)_{12}$— | —H | CCl | meta |
| Iy | —$CH_2CH_3$ | —H | —$(CH_2)_4$— | —H | CCl | para |
| Iz | —$CH_2CH_3$ | —H | —$(CH_2)_4$— | —H | CCl | meta |
| Iaa | —OH | —H | —$(CH_2)_4$— | —H | CCl | para |
| Iab | —OH | —H | —$(CH_2)_4$— | —H | CCl | meta |
| Iac | —$C(CH_3)_2COOH$ | —H | —$(CH_2)_4$— | —H | CCl | para |
| Iad | —$C(CH_3)_2COOH$ | —H | —$(CH_2)_4$— | —H | CCl | meta |
| Iae | —$CH_2CH_2F$ | —H | —$(CH_2)_4$— | —H | CCl | para |
| Iaf | —$CH_2CH_2F$ | —H | —$(CH_2)_4$— | —H | CCl | meta |
| Iag | -cyclopentyl | —H | —$(CH_2)_4$— | —H | CCl | meta |
| Iah | -cyclopentyl | —H | —$(CH_2)_4$— | —H | CCl | para |
| Iai | —$CH_3$ | —$CH_3$ | —$(CH_2)_4$— | —H | CCl | para |
| Iaj | —$CH_3$ | —$CH_3$ | —$(CH_2)_4$— | —H | CCl | meta |
| Iak | —$CH_3$ | —H | —$(CH_2)_4$— | —$CH_3$ | CCl | para |
| Ial | —$CH_3$ | —H | —$(CH_2)_4$— | —$CH_3$ | CCl | meta |
| Iam | —$CH_3$ | —H | —$(CH_2)_4$— | —H | N | para |
| Ian | —$CH_3$ | —H | —$(CH_2)_4$— | —H | N | meta |
| Iao | —$CH_2CH_3$ | —H | —$(CH_2)_4$— | —H | N | para |
| Iap | —$CH_2CH_3$ | —H | —$(CH_2)_4$— | —H | N | meta |
| Iaq | —OH | —H | —$(CH_2)_4$— | —H | N | para |
| Iar | —OH | —H | —$(CH_2)_4$— | —H | N | meta |
| Ias | —$C(CH_3)_2COOH$ | —H | —$(CH_2)_4$— | —H | N | para |
| Iat | —$C(CH_3)_2COOH$ | —H | —$(CH_2)_4$— | —H | N | meta |
| Iau | —$CH_2CH_2F$ | —H | —$(CH_2)_4$— | —H | N | para |
| Iav | —$CH_2CH_2F$ | —H | —$(CH_2)_4$— | —H | N | meta |
| Iaw | -cyclopentyl | —H | —$(CH_2)_4$— | —H | N | meta |
| Iax | -cyclopentyl | —H | —$(CH_2)_4$— | —H | N | para |
| Iay | —$CH_3$ | —$CH_3$ | —$(CH_2)_4$— | —H | N | para |
| Iaz | —$CH_3$ | —$CH_3$ | —$(CH_2)_4$— | —H | N | meta |
| Iba | —$CH_3$ | —H | —$(CH_2)_4$— | —$CH_3$ | N | para |
| Ibb | —$CH_3$ | —H | —$(CH_2)_4$— | —$CH_3$ | N | meta |

While not intending to be limited by theory, the compounds of formulas I are believed to inhibit bacterial cell wall biosynthesis, thereby inhibiting the growth of the bacteria or causing lysis of the bacteria. Accordingly, compound of formula I are useful as antibiotics.

Among other properties, compounds of the invention have been found to possess surprising and unexpected potency against Gram-positive bacteria, including methicillin-resistant *Staphylococci aureus* (MRSA), as described further herein below.

General Synthetic Procedures

The cross-linked glycopeptide—cephalosporin compounds of this invention can be prepared from readily available starting materials, such as the intermediate compounds 1–3 described herein. It will be appreciated that where typical or preferred process conditions (i.e., reaction temperatures, times, mole ratios of reactants, solvents, pressures, etc.) are given, other process conditions can also be used, as determined by one skilled in the art, unless otherwise stated. Optimum reaction conditions may vary with the particular reactants or solvent used, but such conditions can be readily determined by one skilled in the art by routine optimization procedures.

Additionally, as will be apparent to those skilled in the art, conventional protecting groups may be necessary or desired to prevent certain functional groups from undergoing undesired reactions. Suitable protecting groups for a particular functional group, as well as suitable conditions for protection and deprotection of such functional groups, are well known in the art. Protecting groups other than those illustrated in the procedures described herein may be used, if desired. For example, numerous protecting groups, and means for their introduction and removal, are described in T. W. Greene and G. M. Wuts, *Protecting Groups in Organic Synthesis*, Third Edition, Wiley, N.Y., 1999, and references cited therein.

In one method of synthesis, the compounds of formula I are prepared by reacting a compound of formula 1:

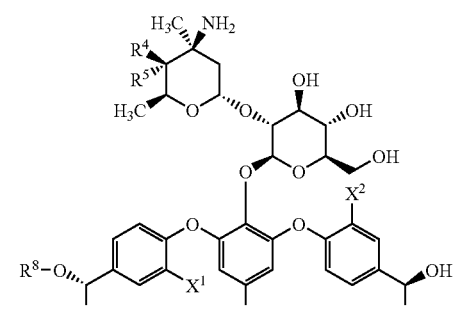

-continued

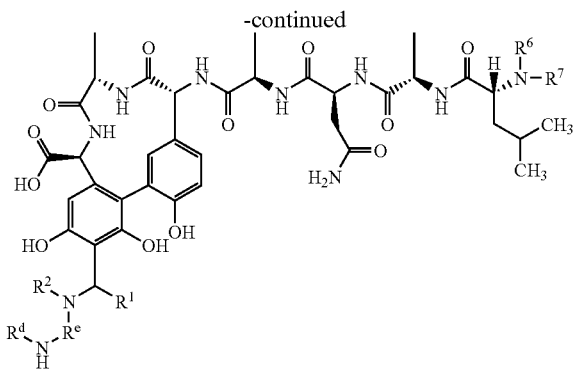

where $R^1$–$R^8$, $R^d$, $R^e$ $X^1$ and $X^2$ are as defined herein, or a salt, or an activated and/or protected derivative thereof, with a compound of formula 2:

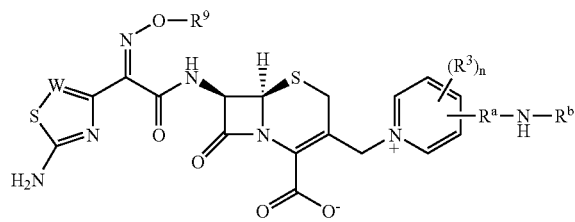

2 where W, $R^3$, $R^9$, $R^{a-e}$, and n are as defined herein, or a salt or carboxy-protected derivative thereof; in the presence of a compound of formula 3:

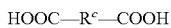

3 or a salt, activated derivative, or protected derivative thereof, wherein $R^c$ is as defined herein; to form the compound of formula I, or a salt or protected derivative thereof. Preferred embodiments of the variables in 1, 2 and 3 are as described herein.

In preparing compounds of formula II, variables in structures 1, 2, and/or 3 are defined as follows: n is 0; $R^a$ is $CH_2$; $R^b$ is hydrogen, $C_{1-4}$ alkyl or $C_{2-4}$ alkenyl (as defined for $R^{10}$ above); $R^c$ is $C_{1-12}$ alkylene or $C_{2-12}$ alkenylene (as defined for $R^{11}$ above); $R^2$, $R^5$, and $R^6$ are hydrogen; $R^7$ and $R^9$ are $CH_3$; $R^4$ is OH; and $X^1$ and $X^2$ are chloro.

Figure 3:
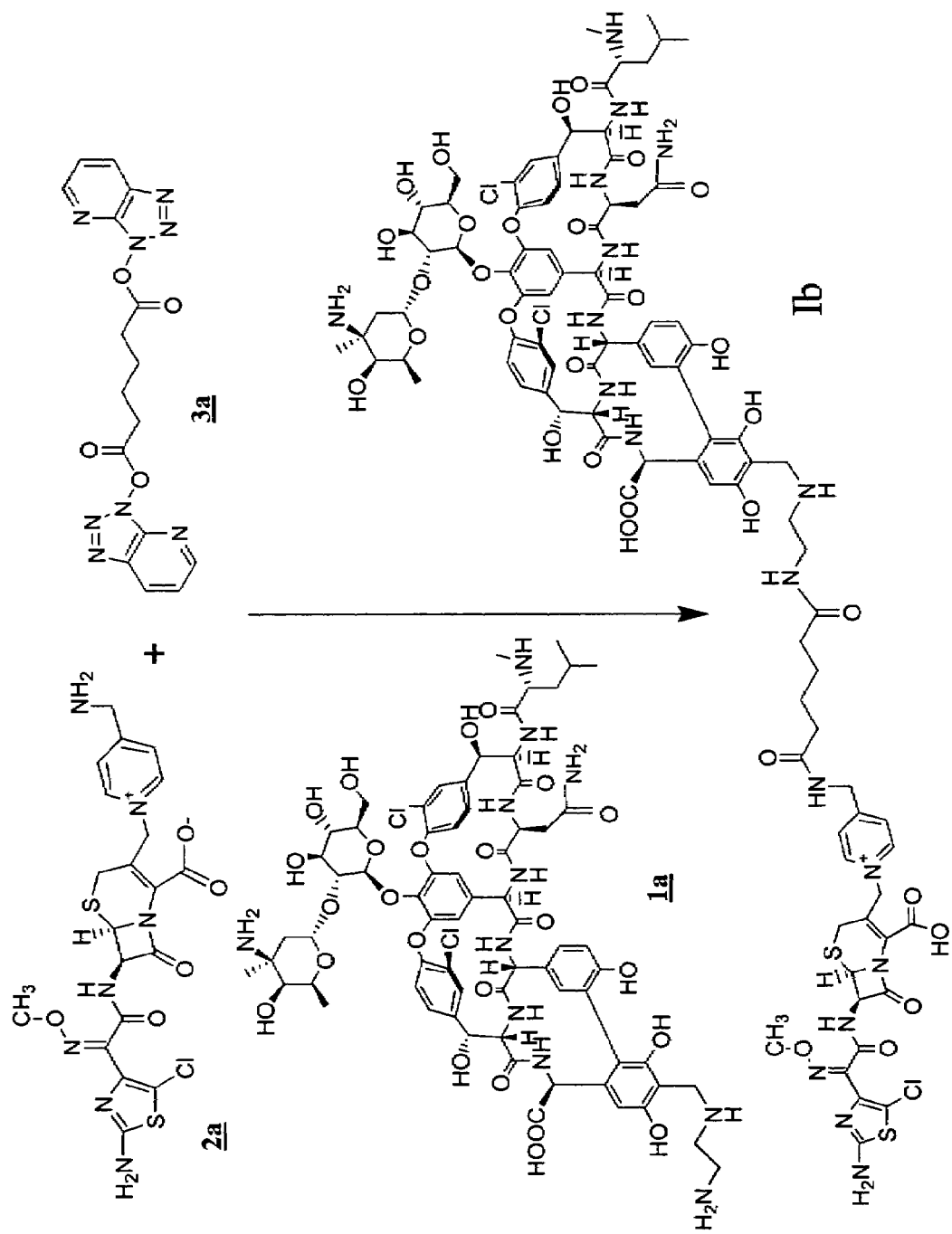
FIG. 3 shows a representative process for preparing cross-linked glycopeptide—cephalosporin antibiotics of the invention.

Typically, for preparing compounds of formula I in which x=y=1, a lactam intermediate 2, having a primary or secondary amino group (—$R^a$—$NHR^b$) as shown, is reacted with an excess of bifunctional linking reagent 3, with the latter in activated form (see FIG. 3). Employing an excess of 3 (typically a 3- to 10-fold molar excess; e.g. a 5-fold molar excess, as shown in Example 3) favors formation of the monoadduct of 2 and 3, rather than a bis-adduct of 3 with two molecules of 2. Preferably, 3 is provided as an activated derivative, such as the bis-HOAT derivative, and the reaction is catalyzed with an amine such as 2,4,6-collidine. The adduct is then reacted with about 0.5 to about 2.5 equivalents, preferably about 1.5 equivalents, relative to original lactam 3, of glycopeptide 1, or a salt thereof, in an inert solvent, such as DMF, containing a catalyst such as 2,4,6-collidine. The coupling reactions are generally carried out at a temperature ranging from about –20° C. to about 25° C., preferably in an ice bath (about 0–4° C.), for about 15 minutes to 3 hours, or until the reaction is substantially complete.

Intermediates of formula 1 can in turn be prepared by Mannich reaction (aminoalkylation) of the phenolic A-ring on a vancomycin-type glycopeptide, employing the desired diamine (HR$^2$N—R$^e$—NHR$^d$), an aldehyde (R$^1$CHO, preferably where R$^1$=H) and base, as described in Example 2. Glycopeptides for preparation of the intermediates of formula 1 are either commercially available or can be prepared by fermentation of the appropriate glycopeptide-producing organism, followed by isolation of the glycopeptide from the resulting fermentation broth using art recognized procedures and equipment.

Figure 2:
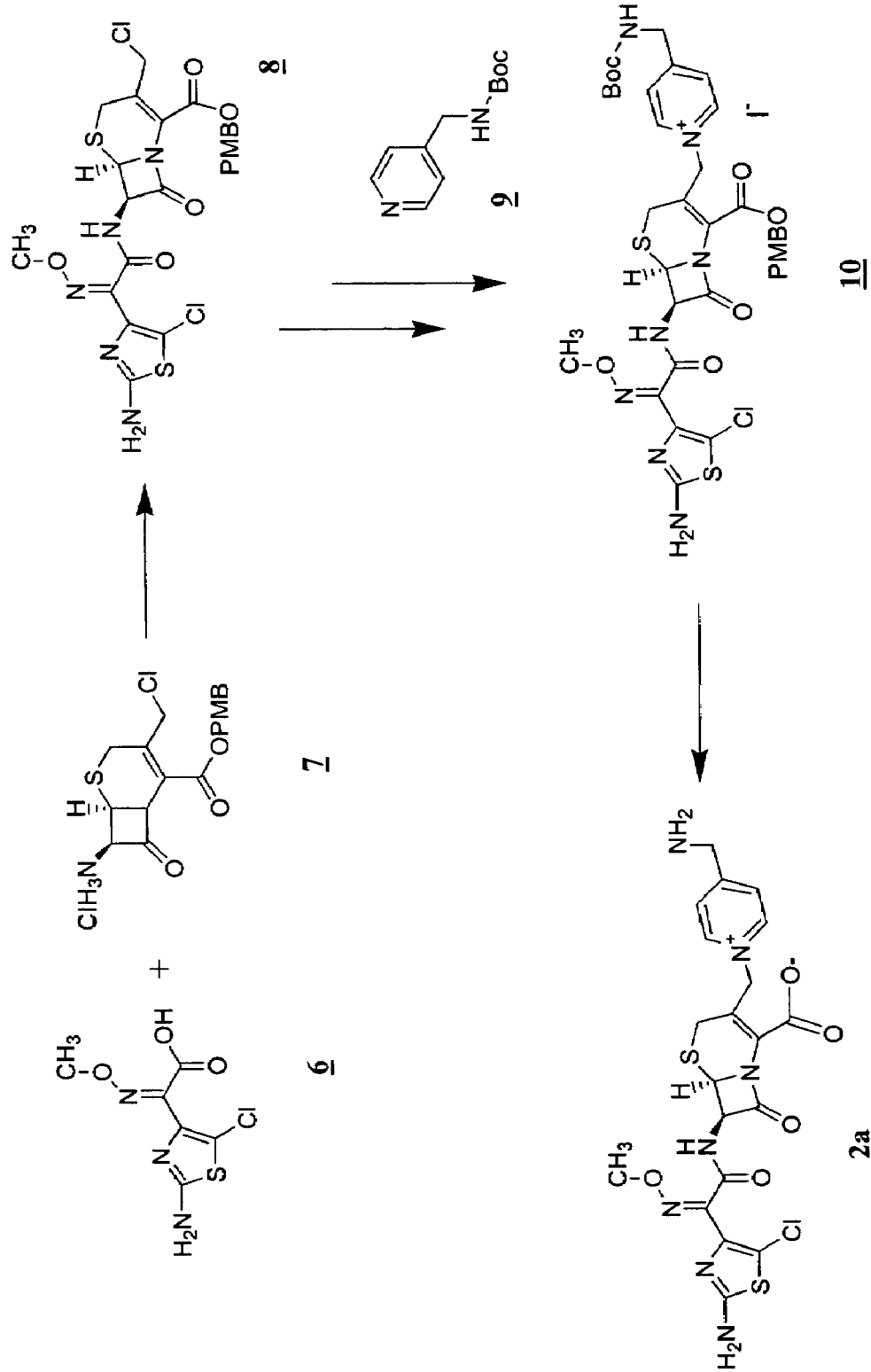
FIG. 2 shows a representative process for preparing cephalosporin intermediates that are useful as intermediates for the compounds of the invention.

The cephalosporin intermediate 2 is readily prepared from commercially available starting materials and reagents using conventional procedures. By way of example, an intermediate of formula 2 can be prepared as shown in FIG. 2 and described in Example 1. Briefly, 2-amino-5-chloro-α-methoxyimino-4-thiazole acetic acid, shown at 6 in FIG. 2, was reacted with the amino cephalosporinic ester 7, catalyzed with EDAC, forming an amide linkage. This product (8) was reacted with sodium iodide in acetone, followed by displacement of the primary iodide with a protected aminoalkyl pyridine derivative. The pyridine derivative contains optional substituent(s) $R^3$, as shown in structure 2 above. In the preparation shown in FIG. 2, the compound 4-(N-tert-BOC amino)methyl pyridine (9) is employed, such that $R^a$ is methylene and $R^b$ is hydrogen. This reaction gives intermediate (10) in protected form; deprotection with TFA/anisole gives intermediate 2a (intermediate 2 where W is CCl, $R^9$ is Me, n is 0, $R^a$ is $CH_2$ and $R^b$ is hydrogen).

For preparing compounds of formula I where x=0, an intermediate such as a compound of formula 4:

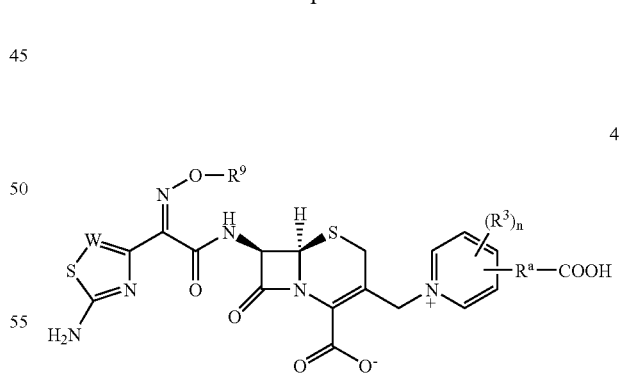

4 wherein $R^a$, $R^3$, $R^9$, W and n are as defined herein; is condensed with an intermediate of formula 1. Intermediate 4 can be prepared by a varation of the procedure given in Example 1, where a pyridine derivative substituted with a protected carboxalkyl group (—$R^a$COOH) is used in place of the aminoalkyl substituted pyridine.

For preparing compounds of formula I where y=0, a glycopeptide derivative of formula 5:

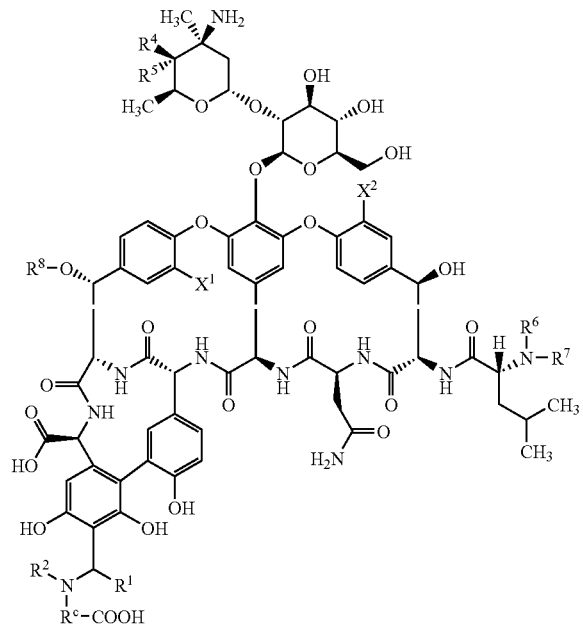

where $R^1$–$R^8$, $R^c$, $X^1$ and $X^2$ are as defined herein, or a salt, or an activated and/or protected derivative thereof (i.e., formula 1 where —$NHR^2$—$R^e$—$NHR^d$ is replaced with —$NHR^2$—$R^e$—COOH) is condensed with an intermediate of formula 2. Intermediates of formula 5 may be prepared according to variation of the preparation shown in Example 2, where an amino acid ($R^2$HN—$R^e$—COOH, in carboxy-protected form), rather than a diamine, is used in the Mannich reaction (see e.g. J. H. Short and C. W. Ours, *J Heterocyc. Chem.* 12(5):869–76, October 1975).

For preparing compounds of formula I where x>1, one or more amino acids of formula HOOC—$R^c$—$NHR^b$ can be added to the reactive amine (—$R^a$—$NHR^b$) of intermediate 2, prior to reaction with 3 and 1 as described above. Similarly, for preparation of compounds of formula I in which y>1, one or more amino acids of formula HOOC—$R^e$—$NHR^d$ can be added to the reactive amine (—$NHR^2$) of intermediate 1, prior to reaction with the adduct of 2 and 3 as described above.

Preferred coupling reagents, or activating reagents, for use in these reactions include benzotriazol-1-yloxy tripyrrolidinophosphonium hexafluorophosphate (PyBOP), preferably used in the amount of about 0.5 to about 1.5 equivalents, preferably about 0.9 to about 1.1 equivalents, in combination with about 0.5 to about 1.5 equivalents, preferably about 0.9 to about 1.1 equivalents, of 1-hydroxybenzotriazole (HOBT) or 1-hydroxy-7-azabenzotriazole (HOAT). Other suitable coupling reagents include O-(7-azabenzotriazol-1-yl)-N,N,N',N'-tetramethyluronium hexafluorophosphate (HATU); bis(2-oxo-3-oxazolidinyl) phosphinic chloride (BOP-Cl); diphenylphosphoryl azide (DPPA); diphenylphosphinic chloride; diphenyl chlorophosphate (DPCP) and HOAT; 1-(3-dimethylaminopropyl)-3-ethylcarbodiimide hydrochloride (EDAC); pentafluorophenyl diphenylphosphinate, and the like.

After the coupling reaction is complete, any protecting groups present in the product are then removed using conventional procedures and reagents. For example, deprotection of N-trityl, N-BOC (N-tert-butoxycarbonyl) and/or COO-PMB (para-methoxybenzyl ester) can be effected by treatment with excess trifluoroacetic acid and excess anisole or triethylsilane in an inert diluent, such as dichloromethane or heptane, at ambient temperature for about 1 to about 12 hours, or until the reaction is complete. The deprotected product can be purified using conventional procedures, such as column chromatography, HPLC, recrystallization and the like.

Various substituted pyridines for use in the above reactions, or for preparing compounds with varying substitution at $R^a$ and/or $R^3$, as disclosed herein, are either commercially available or can be prepared from commercially available starting materials and reagents using conventional procedures. For example, various aminoalkyl-substituted pyridines are commercially available, e.g. aminomethyl pyridines, where $R^a$ is methylene, and aminoethyl pyridines, where $R^a$ is ethylene, or can be prepared using standard organic synthesis procedures. Representative substituted pyridine derivatives for use in this reaction include those in which $R^3$ is selected from methyl, methoxy, thiomethoxy, carboxythiomethoxy, fluoro, chloro, phenyl, cyclopropyl, carboxylic acid, carboxamide, and combinations thereof. For preparation of compounds in which Y, which links R" to the pyridinium ring, is selected from NR', O (ether), S (sulfide), carbonyl, NR'(CO), and (CO)NR'), starting pyridine compounds are commercially available or can be prepared by well known procedures. For example, 3-hydroxypyridine, 4-hydroxypyridine, 3-aminopyridine, 4-aminopyridine, 4-mercaptopyridine, nicotinic acid and isonicotinic acid are commerically available from Aldrich Chemical Co, Milwaukee, Wis.

In preparing compounds in which Y', in the linker group $R^c$, is selected from O (ether) and NR' (rather than a direct bond), linking moieties including $R^c$ will include one or more carbamate or urea linkages, rather than amide linkages. Such linkages can be formed by conventional methods. For example, an amine (such as —$NHR^b$ in intermediate 3 can be reacted with an isocyanate or a chloroformate to form, respectively, a urea or carbamate linkage.

Further details regarding specific reaction conditions and procedures for preparing representative compounds of this invention or intermediates thereto are described in the Examples set forth below.

Pharmaceutical Compositions

The cross-linked glycopeptide—cephalosporin compounds of this invention are typically administered to a patient in the form of a pharmaceutical composition. Accordingly, in one of its composition aspects, this invention is directed to a pharmaceutical composition comprising a pharmaceutically-acceptable carrier or excipient and a therapeutically effective amount of a compound of formula I or a pharmaceutically acceptable salt thereof.

Any conventional carrier or excipient may be used in the pharmaceutical compositions of this invention. The choice of a particular carrier or excipient, or combinations of carriers or excipients, will depend on the mode of administration being used to treat a particular patient or type of bacterial infection. In this regard, the preparation of a suitable pharmaceutical composition for a particular mode of administration, such as oral, topical, inhaled or parenteral administration, is well within the scope of those skilled in the pharmaceutical arts. Additionally, the ingredients for such compositions are commercially-available from, for example, Sigma, P.O. Box 14508, St. Louis, Mo. 63178. By way of further illustration, conventional formulation techniques are described in *Remington's Pharmaceutical Sciences*, Mace Publishing Co., Philadelphia, Pa. 17$^{th}$ Ed. (1985) and *"Modern Pharmaceutics,"* Marcel Dekker, Inc. 3$^{rd}$ Ed. (G. S. Banker & C. T. Rhodes, Eds.).

The pharmaceutical compositions of this invention will typically contain a therapeutically effective amount of a compound of formula I or a pharmaceutically-acceptable salt thereof. Typically, such pharmaceutical compositions will contain from about 0.1 to about 90% by weight of the active agent, and more generally from about 10 to about 30% of the active agent.

Preferred pharmaceutical compositions of this invention are those suitable for parenteral administration, particularly intravenous administration. Such pharmaceutical compositions typically comprise a sterile, physiologically-acceptable aqueous solution containing a therapeutically effective amount of a compound of formula I or a pharmaceutically-acceptable salt thereof.

Physiologically-acceptable aqueous carrier solutions suitable for intravenous administration of active agents are well-known in the art. Such aqueous solutions include, by way of example, 5% dextrose, Ringer's solutions (lactated Ringer's injection, lactated Ringer's plus 5% dextrose injection, acylated Ringer's injection), Normosol-M, Isolyte E, and the like.

Optionally, such aqueous solutions may contain a co-solvent, for example, polyethylene glycol; a chelating agent, for example, ethylenediamine tetraacetic acid; a solubilizing agent, for example, a cyclodextrin; an anti-oxidant, for example, sodium metabisulphite; and the like.

If desired, the aqueous pharmaceutical compositions of this invention can be lyophilized and subsequently reconstituted with a suitable carrier prior to administration. In a preferred embodiment, the pharmaceutical composition is a lyophilized composition comprising a pharmaceutically-acceptable carrier and a therapeutically effective amount of a compound of formula I, or a pharmaceutically-acceptable salt thereof. Preferably, the carrier in this composition comprises sucrose, mannitol, dextrose, dextran, lactose or a combination thereof. More preferably, the carrier comprises sucrose, mannitol, or a combination thereof.

In one embodiment, the pharmaceutical compositions of this invention contain a cyclodextrin. When used in the pharmaceutical compositions of this invention, the cyclodextrin is preferably hydroxypropyl-β-cyclodextrin or sulfobutyl ether β-cyclodextrin. In such formulations, the cyclodextrin will comprise about 1 to 25 weight percent; preferably, about 2 to 10 weight percent of the formulation. Additionally, the weight ratio of cyclodextrin to active agent will typically range from about 1:1 to about 10:1.

The pharmaceutical compositions of this invention are preferably packaged in a unit dosage form. The term "unit dosage form" means a physically discrete unit suitable for dosing a patient, i.e., each unit containing a predetermined quantity of active agent calculated to produce the desired therapeutic effect either alone or in combination with one or more additional units. For example, such unit dosage forms may be packaged in sterile, hermetically-sealed ampoules and the like.

The following formulations illustrate representative pharmaceutical compositions of the present invention:

Formulation Example A

A frozen solution suitable for preparing an injectable solution is prepared as follows:

| Ingredients | Amount |
| --- | --- |
| Compound of the Invention | 10 to 1000 mg |
| Excipients (e.g., dextrose) | 0 to 50 g |
| Water for Injection Solution | 10 to 100 mL |

Representative Procedure: The excipients, if any, are dissolved in about 80% of the water for injection and the active compound is added and dissolved. The pH is adjusted with 1 M sodium hydroxide to 3 to 4.5 and the volume is then adjusted to 95% of the final volume with water for injection. The pH is checked and adjusted, if necessary, and the volume is adjusted to the final volume with water for injection. The formulation is then sterile filtered through a 0.22 micron filter and placed into a sterile vial under aseptic conditions. The vial is capped, labeled and stored frozen.

Formulation Example B

A lyophilized powder suitable for preparing an injectable solution is prepared as follows:

| Ingredients | Amount |
| --- | --- |
| Compound of the Invention | 10 to 1000 mg |
| Excipients (e.g., mannitol and/or sucrose) | 0 to 50 g |
| Buffer Agent (e.g., citrate) | 0 to 500 mg |
| Water for Injection | 10 to 100 mL |

Representative Procedure: The excipients and/or buffering agents, if any, are dissolved in about 60% of the water for injection. The active compound is added and dissolved and the pH is adjusted with 1 M sodium hydroxide to 3 to 4.5 and the volume is adjusted to 95% of the final volume with water for injection. The pH is checked and adjusted, if necessary, and the volume is adjusted to the final volume with water for injection. The formulation is then sterile filtered through a 0.22 micron filter and placed into a sterile vial under aseptic conditions. The formulation is then freeze-dried using an appropriate lyophilization cycle. The vial is capped (optionally under partial vacuum or dry nitrogen), labeled and stored under refrigeration.

Formulation Example C

An injectable solution for intravenous administration to a patient is prepared from Formulation Example B above as follows:

Representative Procedure: The lyophilized powder of Formulation Example B (e.g., containing 10 to 1000 mg of active compound) is reconstituted with 20 mL of sterile water and the resulting solution is further diluted with 80 mL of sterile saline in a 100 mL infusion bag. The diluted solution is then administered to the patient intravenously over 30 to 120 minutes.

Utility

The cross-linked glycopeptide—cephalosporin compounds of the invention are useful as antibiotics. For example, the compounds of this invention are useful for treating or preventing bacterial infections and other bacteria-related medical conditions in mammals, including humans and their companion animals (i.e., dogs, cats, etc.), that are caused by microorganisms susceptible to the compounds of this invention.

Accordingly, in one of its method aspects, the invention provides a method of treating a bacterial infection in a mammal, the method comprising administering to a mammal in need of such treatment, a pharmaceutical composition comprising a pharmaceutically-acceptable carrier and a therapeutically effective amount of a compound of formula I, or a pharmaceutically-acceptable salt thereof.

By way of illustration, the compounds of this invention are particularly useful for treating or preventing infections caused by Gram-positive bacteria and related microorganisms. For example, the compounds of this invention are effective for treating or preventing infections caused by certain *Enterococcus* spp.; *Staphylococcus* spp., including coagulase negative staphylococci (CNS); *Streptococcus* spp.; *Listeria* spp.; *Clostridium* ssp.; *Bacillus* spp.; and the like. Examples of bacterial species effectively treated with the compounds of this invention include, but are not limited to, methicillin-resistant *Staphylococcus aureus* (MRSA); methicillin-susceptible *Staphylococcus aureus* (MSSA); glycopeptide intermediate-susceptible *Staphylococcus aureus* (GISA); methicillin-resistant *Staphylococcus epidermitis* (MRSE); methicillin-sensitive *Staphylococcus epidermitis* (MSSE); vancomycin-sensitive *Enterococcus faecalis* (EFSVS); vancomycin-sensitive *Enterococcus faecium* (EFMVS); penicillin-resistant *Streptococcus pneumoniae* (PRSP); *Streptococcus pyogenes*; and the like.

As shown in Table II of Example 6 below, compounds Ia–c were more effective than vancomycin, by a factor of 10 or more, against methicillin-sensitive *Staphylococcus aureus* and methicillin-resistant *Staphylococcus aureus*. Compound Ic was also significantly more active than its des-chloro analog "des-Cl Ic," although this compound was also more active than vancomycin against MSSA. In a "time-kill" assay, as described in Example 7, a compound of formula I, i.e. compound Ib, was bactericidal against MRSA at a concentration of 1.0 µg/mL in 4 hours. By comparison, vancomycin was bactericidal against MRSA at a concentration of 4 µg/mL in 24 hours. In an in vivo assay in neutropenic mice, as described in Example 8, a compound of formula I, i.e. compound Ib, had an $ED_{50}$ of less than 0.1 mg/kg, iv, compared to an $ED_{50}$ of 9 mg/kg, iv, for vancomycin.

In general, the compounds of the invention are preferred for treating or preventing infections caused by strains of bacteria which are susceptible to either glycopeptides or cephalosporins.

Representative types of infections or bacteria-related medical conditions which can be treated or prevented with the compounds of this invention include, but are not limited to, skin and skin structure infections, urinary tract infections, pneumonia, endocarditis, catheter-related blood stream infections, osteomyelitis, and the like. In treating such conditions, the patient may already be infected with the microorganism to be treated or merely be susceptible to infection in which case the active agent is administered prophylactically.

The compounds of this invention are typically administered in a therapeutically effective amount by any acceptable route of administration. Preferably, the compounds are administered parenterally. The compounds may be administered in a single daily dose or in multiple doses per day. The treatment regimen may require administration over extended periods of time, for example, for several days or for one to six weeks or longer. The amount of active agent administered per dose or the total amount administered will typically be determined by the patient's physician and will depend on such factors as the nature and severity of the infection, the age and general health of the patient, the tolerance of the patient to the active agent, the microorganism(s) causing the infection, the route of administration and the like.

In general, suitable doses will range of from about 0.25 to about 10.0 mg/kg/day of active agent, preferably from about 0.5 to about 2 mg/kg/day. For an average 70 kg human, this would amount to about 15 to about 700 mg per day of active agent, or preferably about 35 to about 150 mg per day.

Additionally, the compounds of this invention are effective for inhibiting the growth of bacteria. In this embodiment, bacteria are contacted either in vitro or in vivo with a growth-inhibiting amount of a compound of formula I or pharmaceutically-acceptable salt thereof. Typically, a growth-inhibiting amount will range from about 0.008 µg/mL to about 50 µg/mL; preferably from about 0.008 µg/mL to about 25 µg/mL; and more preferably, from about 0.008 µg/mL to about 10 µg/mL. Inhibition of bacterial growth is typically evidenced by a decrease or lack of reproduction by the bacteria and/or by lysis of the bacteria, i.e., by a decrease in colony-forming units in a given volume (i.e., per mL) over a given period of time (i.e., per hour) compared to untreated bacteria.

The compounds of this invention are also effective for inhibiting cell wall biosynthesis in bacteria. In this embodiment, bacterial are contacted either in vitro or in vivo with a cell wall biosynthesis-inhibiting amount of a compound of formula I or pharmaceutically-acceptable salt thereof. Typically, a cell wall biosynthesis-inhibiting amount will range from about 0.04 µg/mL to about 50 µg/mL; preferably from about 0.04 µg/mL to about 25 µg/mL; and more preferably, from about 0.04 µg/mL to about 10 µg/mL. Inhibition of cell wall biosynthesis in bacteria is typically evidenced by inhibition or lack of growth of the bacteria including lysis of the bacteria.

Additionally, compounds of this invention have been found to have surprising and unexpectedly rapid cidality against certain bacteria, including methicillin-resistant *Staphylococci aureus* (MRSA) and methicillin-resistant *Staphylococci epidermitis* (MRSE). These properties, as well as the antibiotic utility of the compounds of this invention, can be demonstrated using various in vitro and in vivo assays well-known to those skilled in the art. For example, representative assays are described in further detail in the following Examples.

EXAMPLES

The following synthetic and biological examples are offered to illustrate this invention and are not to be construed in any way as limiting the scope of this invention.

In the examples below, the following abbreviations have the following meanings unless otherwise indicated. Abbreviations not defined below have their generally accepted meaning.

| | |
|---|---|
| BOC = | tert-butoxycarbonyl |
| CFU = | colony-forming units |

-continued

| | |
|---|---|
| DCM = | dichloromethane |
| DIPEA = | diisopropylethylamine |
| DMF = | N,N-dimethylformamide |
| DMSO = | dimethyl sulfoxide |
| EtOAc = | ethyl acetate |
| HOBT = | 1-hydroxy benzotriazole |
| HOAT = | 1-hydroxy-7-azabenzotriazole |
| HPLC = | high performance liquid chromatography |
| MIC = | minimum inhibitory concentration |
| MS = | mass spectrometry |
| PMB = | p-methoxybenzyl |
| PyBOP = | benzotriazol-1-yloxytripyrrolidino-phosphonium hexafluorophosphate |
| THF = | tetrahydrofuran |
| TLC = | thin layer chromatography |
| TFA = | trifluoroacetic acid |

All temperatures reported in the following examples are in degrees Celsius (° C.) unless otherwise indicated. Also, unless noted otherwise, reagents, starting materials and solvents were purchased from commercial suppliers (such as Aldrich, Fluka, Sigma and the like) and were used without further purification. Vancomycin hydrochloride semi-hydrate was purchased from Alpharma, Inc., Fort Lee, N.J. 07024 (Alpharma AS, Oslo, Norway).

Reverse-phase HPLC was typically conducted using a $C_{18}$ column and (A) 98% water, 2% acetonitrile, 0.1% TFA, with an increasing gradient (e.g., 0 to about 70%) of (B) 10% water, 90% acetonitrile, 0.1% TFA, unless otherwise stated.

Example 1

Preparation of 2a: (7R)-7-[(Z)-2-(2-Amino-5-chlorothiazol-4-yl)-2-(methoxyimino)acetamido]-3-[(4-(aminomethyl)-1-pyridinio)methyl]-3-cephem-4-carboxylate Bis-trifluoroacetic Acid Salt (see FIG. 2)

A. Preparation of 2-Amino-5-Chloro-α-(Methoxyimino)-4-Thiazoleacetic Acid (6)

To 500 mL of DMF were added 50.0 g (250 mmol) of 2-amino-α-(methoxyimino)-4-thiazoleacetic acid and 35 g (260 mmol) of N-chlorosuccinimide. The mixture was stirred at room temperature overnight, after which time mass spectral analysis showed no more starting material to be present. The light brown solution was used without further purification.

B. Preparation of Cephalosporin Derivative (8)

To the solution of the acid 6 in DMF from Step (a) was added 101.5 g (250 mmol) of the aminocephalosporonic ester 7, 34 g (250 mmol). The mixture was cooled to 0° C., and 33.5 mL (250 mmol) of 2,4,6-collidine was added. To this solution was added 53 g (275 mmol) of 1-(3-dimethylaminopropyl)-3-ethylcarbodiimide hydrochloride. After 2 hours, the solution was precipitated into 3 L water and filtered. The solids were washed with water (2×1 L), saturated sodium bicarbonate (500 mL) and water (4×500 mL) and dried under vacuum. The dried solids were taken up in 500 mL of methylene chloride at room temperature, and the solution was slowly stirred, forming a precipitate. The crystals were collected by filtration, washed with methylene chloride until the washings were no longer brown, and dried under vacuum to give the amide 8 (74 g).

Analytical Data: MS m/z calc. 586.04, obs. 586.2 (M+1); $^1$H NMR (DMSO-$d_6$): δ9.60 (d, 1H), 7.35 (m, 3H), 6.91 (d, 2H), 5.82 (m, 1H), 5.17 (m, 3H), 4.56 (m, 2H), 3.84 (s, 3H) 3.76 (s, 3H), 3.62 (m, 2H).

C. Preparation of Cephalosporin Derivative (10)

Acetone (250 mL) was added to a mixture of 50 g (85 mmol) of the chloromethylcephalosporin ester 8 and 13 g (85 mmol) of sodium iodide, under nitrogen in the dark. After stirring for 30 minutes, 27 g (130 mmol) of 4-(N-tert-butoxycarbonyl)aminomethyl pyridine (9) and 30 mL of acetone were added. After stirring an additional 2 hours, 1.4 L of 0.1N HCl was added, producing a gummy precipitate. The solvent portion was decanted, and the gummy residue was treated with 800 mL of water to give a solid. The water was decanted, and the solid was dissolved in 1 L of 4:1 ethyl acetate/ethanol. The solution was washed with 500 mL of saturated brine, dried over magnesium sulfate, and evaporated to dryness to give 70 g (79 mmol, 93%) of product 10, having a purity of of 78% as determined by HPLC (254 nm).

D. Preparation of Cephalosporin Derivative (2a)

The cephalosporin derivative, 10, was deprotected as follows. The crude product (70 g, 79 mmol) was dissolved in 550 mL of methylene chloride under nitrogen, and 35 mL (320 mmol) of anisole were added, followed by 150 mL of trifluoroacetic acid. After 2 hours, the mixture was concentrated under vacuum. The product precipitated on addition of 1 L of diethyl ether. The solids were isolated by filtration, washed with ether, stirred in 200 mL of water and filtered. The filtrate was lyophilized to dryness and purified by reverse-phase HPLC, yielding 30 g (approx. 50%) of compound 2a, as the bis-TFA salt, which was used without further purification.

Example 2

Preparation of 1a: Formula I where $R^1$, $R^2$, $R^5$, $R^6$, $R^8$=H; $R^4$=OH; $R^7$=Me; $X^1$, $X^2$=Cl; $R^d$=H; and $R^e$=—$CH_2CH_2$—

Under nitrogen, vancomycin hydrochloride monohydrate (20 g, 13 mmol) was dissolved in water (100 mL) and cooled in an ice bath. Ethylenediamine (7 mL, 100 mmol) was added, followed by 1N NaOH (50 mL, 50 mmol). Formaldehyde (1.3 mL 37% aqueous $H_2CO$, 17 mmol) was added and the reaction mixture was kept in the dark at 4° C. overnight. HPLC analysis of the reaction mixture showed 78% of the desired product 1a, plus unreacted vancomycin and a bis-addition product. The reaction mixture was acidified at 4° C. and the product recovered and purified by HPLC.

Example 3

Preparation of Compound Ib (see FIG. 3)

Adipic acid (3 where $R^c$=n-butylene) bis-HOAT ester (3a, 6.5 mmol) was dissolved in DMF (50 mL) and pyridinium lactam bis-trifluoroacetate 2a (1.0 g, 1.3 mmol), prepared as described in Example 1 above, was added. The solution was then cooled in an ice bath and 2,4,6-collidine (342 μL, 2.6 mmol) was added, and the mixture was stirred in the ice bath for 15 minutes, followed by quenching with 300 μL TFA (3.9 mmol). The reaction mixture was then poured into 400 mL of ethyl acetate, and the precipitated solids were collected by centrifugation.

A solution of 3.86 g (1.95 mmol) 1a, prepared as described in Example 2, in DMF (40 mL) was added to the collected solid, and the resulting mixture was cooled in an ice bath, followed by addition of 2,4,6-collidine (1.03 μL, 7.8 mmol). The mixture was stirred in the ice bath for 20 minutes, then trifluoroacetic acid was added (800 μL, 10.4 mmol). The mixture was then poured into acetonitrile (400 mL), and the precipitated solid was purified by reverse-phase HPLC to give the product Ib (740 mg, 0.29 mmol, 22% yield).

Analytical Data: MS m/z 2171.8 (MH$^+$).

Example 4

Preparation of Compounds Ia, Ic, and Id

These compounds were prepared according to the procedures described in Examples 1, 2 and 3, substituting the appropriate starting materials.

Analytical Data:
Compound Ia: MS m/z fragments 1127.7, 1681.6, 1824.8 (MH$^+$);
Compound Ic: MS m/z 2171.5 (MH$^+$); and
Compound des-Cl Ic: The des-chloro derivative of Compound Ic (i.e., where the chloro atom in the thiadiazole ring is replaced with hydrogen) was prepared for comparison purposes: MS m/z 2137.6 (MH$^+$).

Example 5

Determination of Aqueous Solubility

The aqueous solubility of compounds of the invention was determined using the following procedure. A 5 wt. % dextrose buffer solution at pH 2.2 was prepared by adding 1 mL of 1 N hydrochloric acid (Aldrich) to 99 mL of a 5 wt. % aqueous dextrose solution (Baxter). A 1 mg/mL stock solution for calibration standards was then prepared by dissolving 1 mg of the test compound in 1 mL of DMSO. This solution was vortexed for 30 seconds and then sonicated for 10 minutes. The stock solution was then diluted with water to prepare calibration standards having the following concentrations: 50, 125, 250, 375 and 500 μg/mL.

Each test compound (30 mg) was weighed into a Millipore non-sterile, Ultrafree-MC 0.1 μm filter unit (Millipore UFC30VVOO) and a magnetic stir bar was added to each unit. The 5 wt. % dextrose buffer solution (750 μL) was then added to each unit and these mixtures were vortexed for 5 minutes. The filter units were then placed in an Eppendorf tube rack and the tube rack was placed on top of a magnetic stirrer. Each unit was then titrated to pH 3 using 1 N NaOH (VWR) and the resulting solutions centrifuged at 7000 rpms for 5 minutes. Each unit was then diluted 200 fold with 5% dextrose buffer solution and the diluted samples were transferred into auto sampler vials for analysis.

The calibration standards and the test samples were analyzed by reverse-phase HPLC using the following conditions:
Column: Luna 150×4.6 mm; C18; 5μ
Mobile phase: A=5/95, B=95/5, both=MeCN/H$_2$O; 0.1% TFA
Method: 10 m Lido 100 (0–100% B in 6 min)
Injection volume: 20 μL
Wavelength: 214 nm The solubility of each test sample was calculated by comparing the peak area of the test sample to the calibration curve and multiplying by the dilution factor.

According to the above procedure, the solubility of compound Ib in 5% aqueous dextrose buffer at pH 3 was determined to be greater than 7 mg/mL.

Example 6

Determination of Minimal Inhibitory Concentrations (MIC)

Minimal inhibitory concentration (MIC) assays were performed using the broth microdilution method set forth in NCCLS guidelines (see, NCCLS. 2000. *Methods for Dilution Antimicrobial Susceptibility Tests for Bacteria That Grow Aerobically*; Approved Standard—Fifth Ed., Vol. 20, No. 2). Bacterial strains were obtained from the American Type Tissue Culture Collection (ATCC), Stanford University Hospital (SU), Kaiser Permanente Regional Laboratory in Berkeley (KPB), Massachusetts General Hospital (MGH), the Centers for Disease Control (CDC), the San Francisco Veterans' Administration Hospital (SFVA) or the University of California San Francisco Hospital (UCSF). Vancomycin-resistant enterococci were phenotyped as Van A or Van B based on their sensitivity to teicoplanin. Some vancomycin-resistant enterococci genotyped as Van A, Van B, Van C1 or Van C2 were also obtained from the Mayo Clinic.

In this assay, cryopreserved bacterial cultures of reference and clinical strains were streaked for isolation on appropriate agar medium (i.e., Trypticase Soy Agar, Trypticase Soy Agar with defibrinated sheep erthrocytes, Brain Heart Infusion Agar, Chocolate Agar). Following incubation to allow formation of colonies, these plates were sealed with parafilm and stored refrigerated for up to two weeks. For preparation of assay inocula and to ensure low variability, several colonies from a bacterial isolate cultured on the agar plates were pricked with an inoculating loop and aseptically transferred to Mueller-Hinton Broth (supplemented with divalent cations to required levels based on manufacturer's certification). The broth culture was grown overnight at 35° C., diluted in fresh prewarmed broth and grown to log phase; this is equivalent to a 0.5 MacFarland standard or 1×10$^8$ colony forming units per milliliter (CFU/mL). Not all cell suspensions, due to species variability, contained 1×10$^8$ CFU/mL when turbidity is equivalent to the MacFarland standard, therefore acceptable adjustments (based on NCCLS guidelines) were made in dilutions of different bacterial strains. The inoculum was diluted such that 100 μL of this culture in Mueller-Hinton Broth, supplemented Mueller-Hinton Broth, or Haemophilus test medium, when over layered onto a 2-fold serially diluted series of antibiotic concentrations also in 100 μL of corresponding medium, in a 96-well microtiter plate resulted in a starting bacterial concentration of 5×10$^5$ CFU/mL. The plates were then incubated 18–24 hours at 35° C. The MIC was read visually as the lowest concentration well with no bacterial growth. Bacterial growth is defined as more than three pinpoint colonies, a button of precipitated cells larger than 2 mm in diameter, or obvious turbidity.

Strains routinely tested in the initial screen included methicillin-sensitive *Staphylococcus aureus* (MSSA), methicillin-resistant *Staphylococcus aureus* (MRSA), *Staphylococcus aureus* producing penicillinase, methicillin-sensistive *Staphylococcus epidermidis* (MSSE), methicillin-resistant *Staphylococcus epidermidis* (MRSE), vancomycin-sensitive *Enterococcus faecium* (EFMVS), vancomycin-sensitive *Enterococcus faecalis* (EFSVS), vancomycin-resistant *Enterococcus faecium* also resistant to teicoplanin (EFMVR Van A), vancomycin-resistant *Enterococcus faecium* sensistive to teicoplanin (EFMVR Van B), vancomycin-resistant *Enterococcus faecalis* also resistant to teicoplanin (EFSVR Van A), vancomycin-resistant *Enterococcus faecalis* sensitive to teicoplanin (EFSVR Van B), penicillin-sensitive *Streptococcus pneumoniae* (PS SP) and penicillin-resistant *Streptococcus pneumoniae* (PSRP). Because of the inability of PSSP and PSRP to grow well in Mueller-Hinton broth, MICs with those strains were determined using either TS broth supplemented with defibrinated blood or Haemophilus test medium.

Test compounds having significant activity against the strains mentioned above were then tested for MIC values in a larger panel of clinical isolates including the species listed above as well as non-speciated coagulase negative *Staphylococcus* both sensitive and resistant to methicillin (MS-CNS and MR-CNS). Additionally, these test compounds were also assayed for MICs against gram-negative microorganisms, such as *Escherichia coli, Pseudomonas aeruginosa, Klebsiella pneumoniae, Enterobacter cloacae, Acinetobacter baumannii, Haemophilius influenzae* and *Moraxella catarrhalis*.

Table II shows $MIC_{90}$ data for compounds of this invention against methicillin-resistant *S. aureus* (MRSA) and methicillin-susceptible *S. aureus* (MSSA) as compared to the known glycopeptide antibiotic, vancomycin.

TABLE II

Minimum Inhibitory Concentrations (MICs), in µg/mL

| Compound | MIC (µg/mL) | |
|---|---|---|
| | MRSA 33591 | MSSA 13709 |
| Ia | 0.15 | 0.15 |
| Ib | <0.1 | <0.1 |
| Ic | 0.1 | <0.1 |
| des-Cl Ic | 3.13 | <0.1 |
| Vancomycin | 2.0 | 1.0 |

The data in Table II demonstate that compounds of this invention (i.e., Ia, Ib and Ic) had surprising and unexpected antibacterial activity against MRSA 33591 compared to either a des-chloro analog or vancomycin; and that compounds of this invention had suprising and unexpected antibacterial acitivity against MSSA 13709 compared to vancomycin.

Example 7

Time-Kill Assay

This time-kill assay is a method for measuring the rate of bactericidal activity of a test compound. These procedures are similar to those described in V. Lorian, "Antibiotics in Laboratory Medicine", Fourth Edition, Williams and Wilkins (1996), pages 104–105. A rapid time-kill is desirable to quickly prevent bacterial colonization and reduce host tissue damage.

Bacterial inocula were prepared as described in Example 6 for determination of MIC. Bacteria were diluted in pre-warmed media in shake flasks and incubated with shaking (200 rpm, 35° C.). At 0, 1, 4, and 24 hours samples were withdrawn from the flasks and bacteria were enumerated by plate counting. Subsequent to the initial sampling, a test compound to be assayed was added to the shake flask culture. Plate counts at these intervals previous to and following addition of the compound were expressed graphically in a time-kill curve. Bactericidal activity is defined as a greater than or equal to 3 log decrease (reduction greater than or equal to 99.9%) in bacterial cell numbers by 24 hours.

In this assay, a compound of formula I, i.e. compound Ib, was bactericidal against MRSA 33591 at a concentration of 1.0 µg/mL in 4 hours. By comparison, vancomycin was bactericidal against MRSA 33591 at a concentration of 4 µg/mL in 24 hours.

Example 8

In vivo Efficacy Studies in Neutropenic Mice

Animals (male CD-1 mice, 20–30g) were acquired from Charles Rivers Laboratories (Gilroy, Calif. and allowed access to food and water ad libitum. Neutropenia was induced via 200 mg/kg intraperitoneal (IP) injection of cyclophosphamide given four and two days prior to the inoculation of bacteria.

The organism used was either a susceptible or resistant strain of clinically relevant gram positive pathogens, such as methicillin-susceptible *Staphylococcus aureus* (MSSA 13709) and methicillin-resistant *Staphylococcus aureus* (MRSA 33591). The bacterial inoculum concentration was $\sim 10^6$ CFU/mL. Animals were lightly anesthetized with isoflurane and 50 mL of the bacterial inoculum was injected into the anterior thigh. One hour after the inoculation, animals were dosed intravenously with vehicle or the appropriate dose of the test compound. At 0 hours and 24 hours post-treatment, the animals were euthanized ($CO_2$ asphyxiation) and the anterior and posterior thigh collected aseptically. The thigh was placed into 10 mL sterile saline and homogenized. Dilutions of the homogenate were plated onto triptic soy agar plates which were incubated overnight. The number of bacterial colonies on a given plate was multiplied by the dilution factor, divided by the thigh weight (in grams) and expressed as log CFU/g. $ED_{50}$ (dose required to produce 50% of the maximum reduction in thigh titre) was estimated for each test compound.

In this assay, a compound of formula I, i.e. compound Ib, had an $ED_{50}$ of less than 7 mg/kg, iv, compared to an $ED_{50}$ of 9 mg/kg, iv, for vancomycin.

While the present invention has been described with reference to specific embodiments thereof, it should be understood by those skilled in the art that various changes may be made an equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, to the extent permitted by applicable patent laws and regulations, all publications, patents, and patent documents cited herein are incorporated by reference herein in their entirety to the same extent as if they had been individually incorporated by reference.

What is claimed is:

1. A compound of formula I:

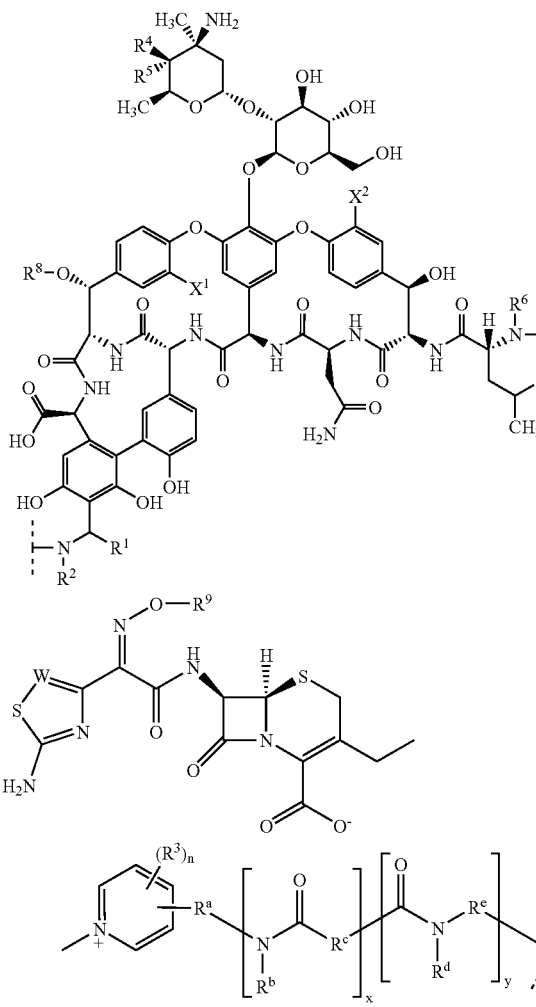

or a pharmaceutically-acceptable salt thereof; wherein
each of $X^1$ and $X^2$ is independently hydrogen or chloro;
W is N or CCl;
$R^1$ and $R^2$ are independently selected from hydrogen and $C_{1-6}$ alkyl;
each $R^3$ is independently selected from $C_{1-6}$ alkyl, OR, halo, —SR, —S(O)R, —S(O)$_2$R, and —S(O)$_2$OR, where each R is independently $C_{1-6}$ alkyl optionally substituted with COOH or 1 to 3 fluoro substituents;
one of $R^4$ and $R^5$ is hydroxy and the other is hydrogen;
$R^6$ and $R^7$ are independently hydrogen or methyl;
$R^8$ is hydrogen or a group of the formula:

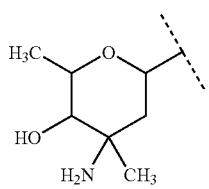

$R^9$ is selected from hydrogen, $C_{1-6}$ alkyl and $C_{3-6}$ cycloalkyl, where alkyl and cycloalkyl are optionally substituted with —COOH or 1 to 3 fluoro substituents;

$R^a$ is —Y—R"—, where R" is selected from $C_{1-12}$ alkylene, $C_{2-12}$ alkenylene, $C_{2-12}$ alkynylene, $C_{3-6}$ cycloalkylene, $C_{6-10}$ arylene, $C_{2-9}$ heteroarylene, $C_{3-6}$ heterocycle and combinations thereof, and is optionally substituted with 1 or 2 groups selected from Z, where each Z is independently selected from the group consisting of —OR', —SR', —F, —Cl, —N(R')$_2$, —OC(O)R', —C(O)OR', —NHC(O)R', —C(O)N(R')$_2$, —CF$_3$, —OCF$_3$, and side chains of naturally-occurring amino acids, where each R' is independently hydrogen or $C_{1-4}$ alkyl; and R" contains at most 20 non-hydrogen atoms; and Y, which links R" to the pyridinium ring at a meta or para position, is selected from a direct bond, NR', O, S, C(O), NR'C(O), and C(O)NR', precluding direct bonds between heteroatoms in Y and R";

each $R^b$ and $R^d$ is independently selected from hydrogen, $C_{1-6}$ alkyl, $C_{2-6}$ alkenyl and $C_{2-6}$ alkynyl;

each $R^c$ is independently a direct bond or —Y'—R"—Y'—, where each Y' is independently selected from a direct bond, O and NR', precluding direct bonds between heteroatoms in Y' and R";

each $R^e$ is independently selected from the group defined by R";

n is an integer from 0 to 3;

x is an integer from 0 to 2; and y is an integer from 0 to 2.

2. The compound of claim 1, wherein $R^9$ is hydrogen, $C_{1-4}$ alkyl or $C_{3-5}$ cycloalkyl, where the alkyl group is optionally substituted with —COOH or 1 to 3 fluoro substituents.

3. The compound of claim 2, wherein $R^9$ is hydrogen, methyl, ethyl, 2-fluoroethyl, 2-carboxyprop-2-yl or cyclopentyl.

4. The compound of claim 1, wherein W is CCl.

5. The compound of claim 1, wherein W is N.

6. The compound of claim 1, wherein each $R^3$ is independently selected from $C_{1-4}$ alkyl, $C_{1-4}$ alkoxy, fluoro and chloro.

7. The compound of claim 1, wherein n is 0.

8. The compound of claim 1, wherein x is 0 and y is 1.

9. The compound of claim 1, wherein x is 1 and y is 0.

10. The compound of claim 1, wherein x is 1 and y is 1.

11. The compound of claim 10, wherein $R^a$ is —Y—R"—, where R" is $C_{1-6}$ alkylene; and Y is a direct bond.

12. The compound of claim 11, wherein $R^b$ and $R^d$ are independently hydrogen or methyl.

13. The compound of claim 12, wherein $R^e$ is $C_{1-4}$ alkylene.

14. The compound of claim 13, wherein $R^c$ is —Y'—R"—Y'—, where each Y' is a direct bond and R" is $C_{1-12}$ alkylene.

15. The compound of claim 1, wherein $R^1$ and $R^2$ are hydrogen.

16. A compound of formula II:

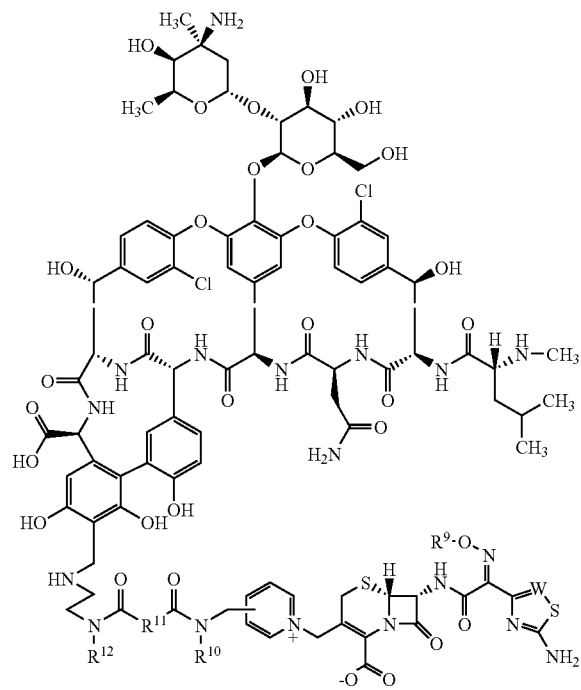

II or a pharmaceutically acceptable salt thereof; wherein
W is N or CCl;
$R^9$ is selected from the group consisting of hydrogen, $C_{1-6}$ alkyl and $C_{3-6}$ cycloalkyl, where alkyl and cycloalkyl are optionally substituted with —COOH or 1 to 3 fluoro substituents;
the pyridinium ring has meta or para substitution;
$R^{10}$ is hydrogen, $C_{1-4}$ alkyl or $C_{2-4}$ alkenyl;
$R^{11}$ is $C_{1-12}$ alkylene or $C_{2-12}$ alkenylene; and
$R^{12}$ is hydrogen, $C_{1-4}$ alkyl or $C_{2-4}$ alkenyl.

17. The compound of claim 16, wherein W is CCl.

18. The compound of claim 16, wherein $R^{10}$ and $R^{12}$ are hydrogen or methyl.

19. The compound of claim 16, wherein $R^{11}$ is $C_{1-10}$ alkylene.

20. The compound of claim 16, wherein W is CCl; $R^9$ is methyl; $R^{10}$ is hydrogen; $R^{11}$ is —(CH$_2$)$_4$—; $R^{12}$ is hydrogen; and the pyridinium ring is para substituted.

21. The compound of claim 16, wherein the compound is selected from:

| $R^9$ | $R^{10}$ | $R^{11}$ | $R^{12}$ | W | Pyridinium Substitution |
|---|---|---|---|---|---|
| —CH$_3$ | —H | —(CH$_2$)$_{10}$— | —H | CCl | para |
| —CH$_3$ | —H | —(CH$_2$)$_4$— | —H | CCl | para |
| —CH$_3$ | —H | —(CH$_2$)$_4$— | —H | CCl | meta |
| —CH$_3$ | —H | —CH$_2$— | —H | CCl | para |
| —CH$_3$ | —H | —CH$_2$— | —H | CCl | meta |
| —CH$_3$ | —H | —(CH$_2$)$_2$— | —H | CCl | para |
| —CH$_3$ | —H | —(CH$_2$)$_2$— | —H | CCl | meta |
| —CH$_3$ | —H | —(CH$_2$)$_3$— | —H | CCl | para |
| —CH$_3$ | —H | —(CH$_2$)$_3$— | —H | CCl | meta |
| —CH$_3$ | —H | —(CH$_2$)$_5$— | —H | CCl | para |
| —CH$_3$ | —H | —(CH$_2$)$_5$— | —H | CCl | meta |
| —CH$_3$ | —H | —(CH$_2$)$_6$— | —H | CCl | para |
| —CH$_3$ | —H | —(CH$_2$)$_6$— | —H | CCl | meta |
| —CH$_3$ | —H | —(CH$_2$)$_7$— | —H | CCl | para |
| —CH$_3$ | —H | —(CH$_2$)$_7$— | —H | CCl | meta |
| —CH$_3$ | —H | —(CH$_2$)$_8$— | —H | CCl | para |
| —CH$_3$ | —H | —(CH$_2$)$_8$— | —H | CCl | meta |
| —CH$_3$ | —H | —(CH$_2$)$_9$— | —H | CCl | para |
| —CH$_3$ | —H | —(CH$_2$)$_9$— | —H | CCl | meta |
| —CH$_3$ | —H | —(CH$_2$)$_{10}$— | —H | CCl | meta |
| —CH$_3$ | —H | —(CH$_2$)$_{11}$— | —H | CCl | para |
| —CH$_3$ | —H | —(CH$_2$)$_{11}$— | —H | CCl | meta |
| —CH$_3$ | —H | —(CH$_2$)$_{12}$— | —H | CCl | para |
| —CH$_3$ | —H | —(CH$_2$)$_{12}$— | —H | CCl | meta |
| —CH$_2$CH$_3$ | —H | —(CH$_2$)$_4$— | —H | CCl | para |
| —CH$_2$CH$_3$ | —H | —(CH$_2$)$_4$— | —H | CCl | meta |
| —OH | —H | —(CH$_2$)$_4$— | —H | CCl | para |
| —OH | —H | —(CH$_2$)$_4$— | —H | CCl | meta |
| —C(CH$_3$)$_2$COOH | —H | —(CH$_2$)$_4$— | —H | CCl | para |
| —C(CH$_3$)$_2$COOH | —H | —(CH$_2$)$_4$— | —H | CCl | meta |
| —CH$_2$CH$_2$F | —H | —(CH$_2$)$_4$— | —H | CCl | para |
| —CH$_2$CH$_2$F | —H | —(CH$_2$)$_4$— | —H | CCl | meta |
| -cyclopentyl | —H | —(CH$_2$)$_4$— | —H | CCl | meta |
| -cyclopentyl | —H | —(CH$_2$)$_4$— | —H | CCl | para |
| —CH$_3$ | —CH$_3$ | —(CH$_2$)$_4$— | —H | CCl | para |
| —CH$_3$ | —CH$_3$ | —(CH$_2$)$_4$— | —H | CCl | meta |
| —CH$_3$ | —H | —(CH$_2$)$_4$— | —CH$_3$ | CCl | para |
| —CH$_3$ | —H | —(CH$_2$)$_4$— | —CH$_3$ | CCl | meta |
| —CH$_3$ | —H | —(CH$_2$)$_4$— | —H | N | para |
| —CH$_3$ | —H | —(CH$_2$)$_4$— | —H | N | meta |
| —CH$_2$CH$_3$ | —H | —(CH$_2$)$_4$— | —H | N | para |
| —CH$_2$CH$_3$ | —H | —(CH$_2$)$_4$— | —H | N | meta |
| —OH | —H | —(CH$_2$)$_4$— | —H | N | para |
| —OH | —H | —(CH$_2$)$_4$— | —H | N | meta |
| —C(CH$_3$)$_2$COOH | —H | —(CH$_2$)$_4$— | —H | N | para |
| —C(CH$_3$)$_2$COOH | —H | —(CH$_2$)$_4$— | —H | N | meta |
| —CH$_2$CH$_2$F | —H | —(CH$_2$)$_4$— | —H | N | para |
| —CH$_2$CH$_2$F | —H | —(CH$_2$)$_4$— | —H | N | meta |
| -cyclopentyl | —H | —(CH$_2$)$_4$— | —H | N | meta |
| -cyclopentyl | —H | —(CH$_2$)$_4$— | —H | N | para |
| —CH$_3$ | —CH$_3$ | —(CH$_2$)$_4$— | —H | N | para |
| —CH$_3$ | —CH$_3$ | —(CH$_2$)$_4$— | —H | N | meta |
| —CH$_3$ | —H | —(CH$_2$)$_4$— | —CH$_3$ | N | para |
| —CH$_3$ | —H | —(CH$_2$)$_4$— | —CH$_3$ | N | meta |

22. A pharmaceutical composition comprising a pharmaceutically acceptable carrier and a therapeutically effective amount of a compound of any one of claims 1 to 21.

23. A method of treating a bacterial infection in a mammal, the method comprising administering to a mammal a pharmaceutical composition comprising a pharmaceutically acceptable carrier and a therapeutically effective amount of a compound of any one of claims 1, 16 or 21.

24. A method of inhibiting the growth of bacteria, the method comprising contacting bacteria with a growth-inhibiting amount of a compound of any one of claims 1, 16 or 21.

25. A method of inhibiting bacterial cell wall biosynthesis, the method comprising contacting bacteria with a cell wall biosynthesis-inhibiting amount of a compound of any one of claims 1, 16 or 21.

26. A process for preparing compound of formula I:
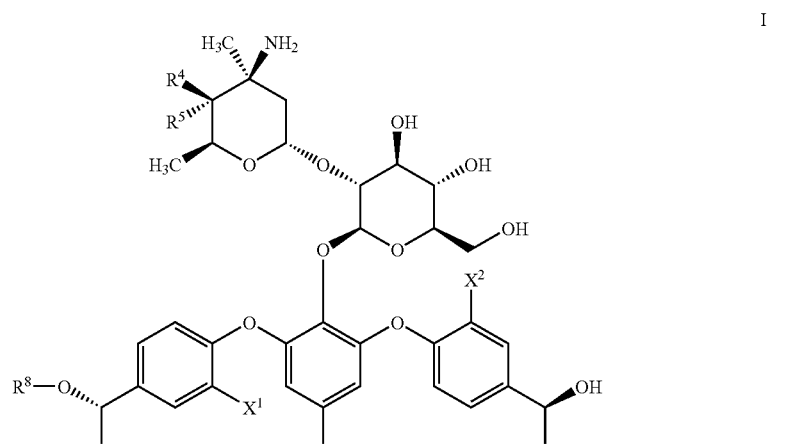
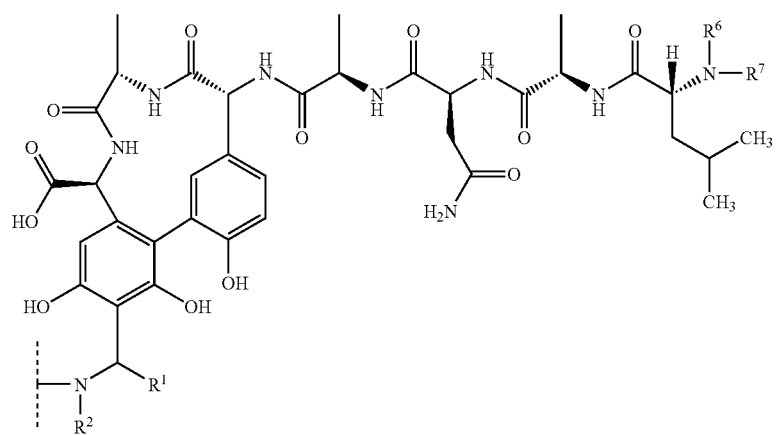
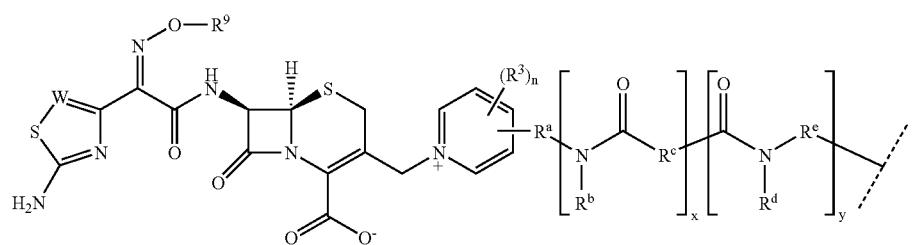

or a salt or protected derivative thereof; wherein
each of $X^1$ and $X^2$ is independently hydrogen or chloro;
W is N or CCl;
$R^1$ and $R^2$ are independently selected from hydrogen and $C_{1-6}$ alkyl;
each $R^3$ is independently selected from $C_{1-6}$ alkyl, OR, halo, —SR, —S(O)R, —S(O)$_2$R, and —S(O)$_2$OR, where each R is independently $C_{1-6}$ alkyl optionally substituted with COOH or 1 to 3 fluoro substituents;
one of $R^4$ and $R^5$ is hydroxy and the other is hydrogen;
$R^6$ and $R^7$ are independently hydrogen or methyl;
$R^8$ is hydrogen or a group of the formula:

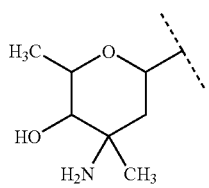

$R^9$ is selected from hydrogen, $C_{1-6}$ alkyl and $C_{3-6}$ cycloalkyl, where alkyl and cycloalkyl are optionally substituted with —COOH or 1 to 3 fluoro substituents;
$R^a$ is —Y—R"—, where R" is selected from $C_{1-12}$ alkylene, $C_{2-12}$ alkenylene, $C_{2-12}$ alkynylene, $C_{3-6}$ cycloalkylene, $C_{6-10}$ arylene, $C_{2-9}$ heteroarylene, $C_{3-6}$ heterocycle and combinations thereof, and is optionally substituted with 1 or 2 groups selected from Z, where each Z is independently selected from the group consisting of —OR', —SR', —F, —Cl, —N(R')$_2$, —OC(O)R', —C(O)OR', —NHC(O)R', —C(O)N(R')$_2$, —CF$_3$, —OCF$_3$, and side chains of naturally-occurring amino acids, where each R' is independently hydrogen or $C_{1-4}$ alkyl; and R" contains at most 20 non-hydrogen atoms; and Y, which links R" to the pyridinium ring at a meta or para position, is selected from a direct bond, NR', O, S, C(O), NR'C(O), and C(O)NR', precluding direct bonds between heteroatoms in Y and R";
each $R^b$ and $R^d$ is independently selected from hydrogen, $C_{1-6}$ alkyl, $C_{2-6}$ alkenyl and $C_{2-6}$ alkynyl;
each $R^c$ is independently a direct bond or —Y'—R"—Y'—, where each Y' is independently selected from a direct bond, O and NR', precluding direct bonds between heteroatoms in Y' and R";
each $R^e$ is independently selected from the group defined by R";
n is an integer from 0 to 3;
x is an integer from 0 to 2; and
y is an integer from 0 to 2:
or a salt thereof, the process comprising comprising reacting a compound of formula 1:

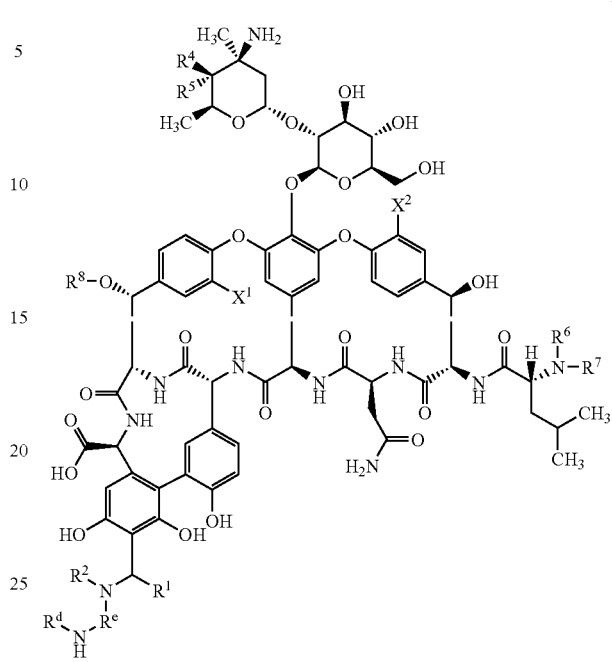

or a salt, or an activated and/or protected derivative thereof, with a compound of formula 2:

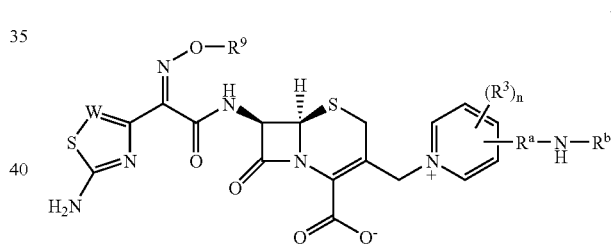

or a salt or carboxy-protected derivative thereof; in the presence of a compound of formula 3:

HOOC—$R^c$—COOH                    3

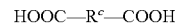

or a salt, activated derivative, or protected derivative thereof; to form the compound of formula I, or a salt or protected derivative thereof.

27. The process of claim 26, wherein the process further comprises forming a pharmaceutically acceptable salt of the compound of formula I.

28. The product prepared by the process of claim 26 or 27.

* * * * *

UNITED STATES PATENT AND TRADEMARK OFFICE
CERTIFICATE OF CORRECTION

PATENT NO.       : 7,067,482 B2
APPLICATION NO.  : 10/888849
DATED            : June 27, 2006
INVENTOR(S)      : Paul R. Fatheree et al.

It is certified that error appears in the above-identified patent and that said Letters Patent is hereby corrected as shown below:

FIGURE AT COLUMN 29 should read:

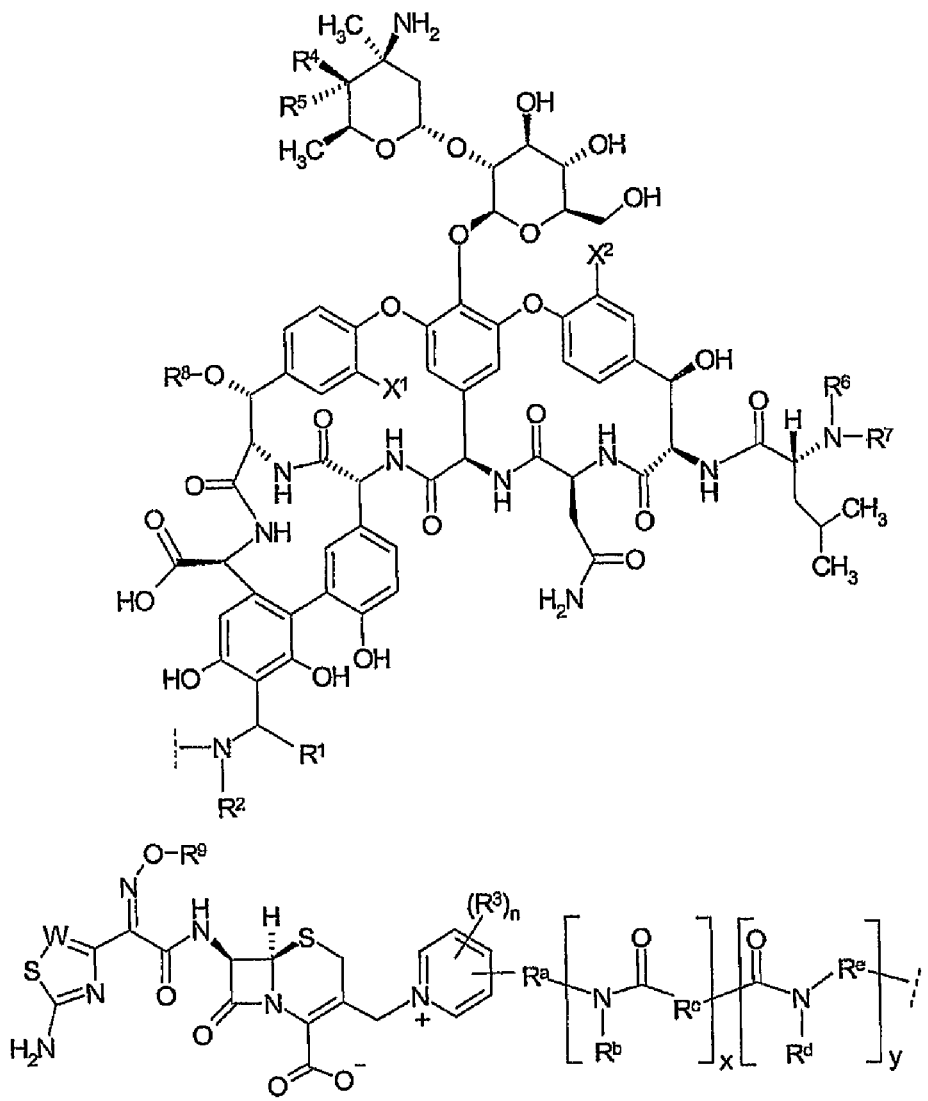

UNITED STATES PATENT AND TRADEMARK OFFICE
CERTIFICATE OF CORRECTION

PATENT NO. : 7,067,482 B2  
APPLICATION NO. : 10/888849  
DATED : June 27, 2006  
INVENTOR(S) : Paul R. Fatheree et al.

Page 2 of 4

It is certified that error appears in the above-identified patent and that said Letters Patent is hereby corrected as shown below:

FIGURE AT COLUMN 31 should read:

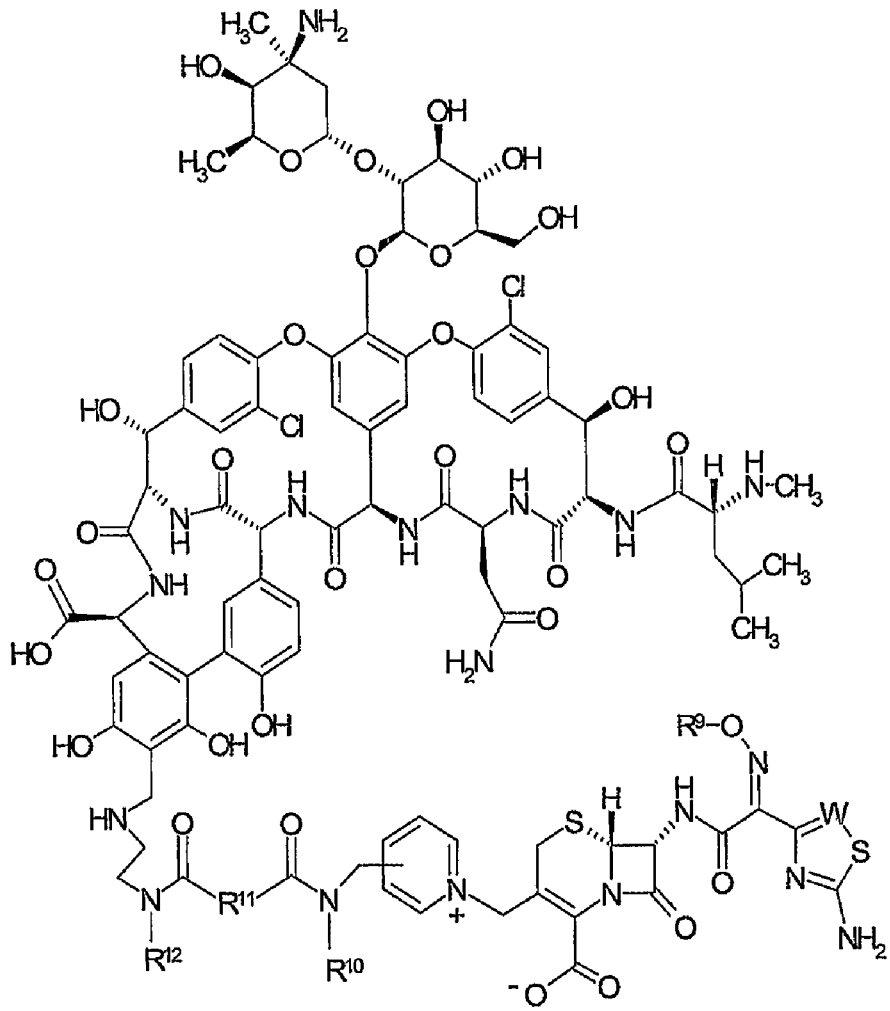

UNITED STATES PATENT AND TRADEMARK OFFICE
CERTIFICATE OF CORRECTION

PATENT NO. : 7,067,482 B2
APPLICATION NO. : 10/888849
DATED : June 27, 2006
INVENTOR(S) : Paul R. Fatheree et al.

It is certified that error appears in the above-identified patent and that said Letters Patent is hereby corrected as shown below:

FIGURE AT COLUMN 33 should read:

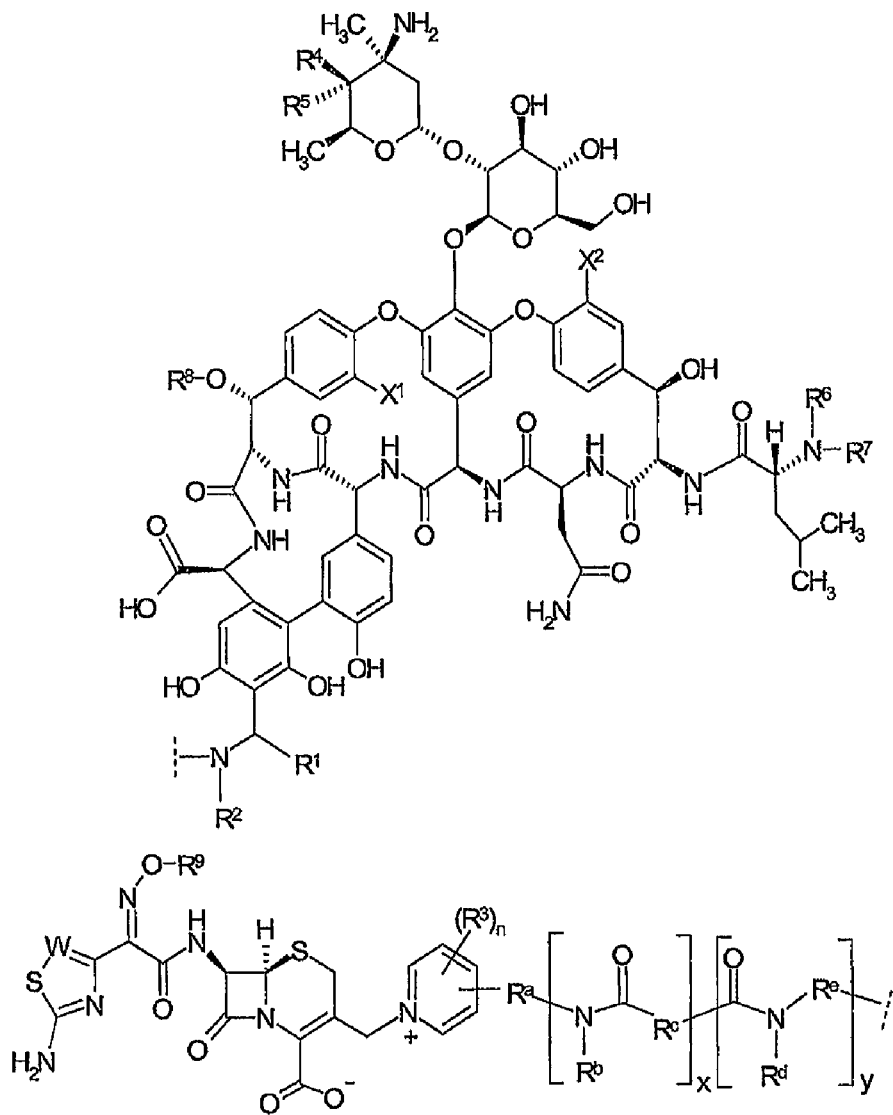

UNITED STATES PATENT AND TRADEMARK OFFICE
CERTIFICATE OF CORRECTION

PATENT NO. : 7,067,482 B2  
APPLICATION NO. : 10/888849  
DATED : June 27, 2006  
INVENTOR(S) : Paul R. Fatheree et al.

Page 4 of 4

It is certified that error appears in the above-identified patent and that said Letters Patent is hereby corrected as shown below:

FIGURE AT COLUMN 36 should read:

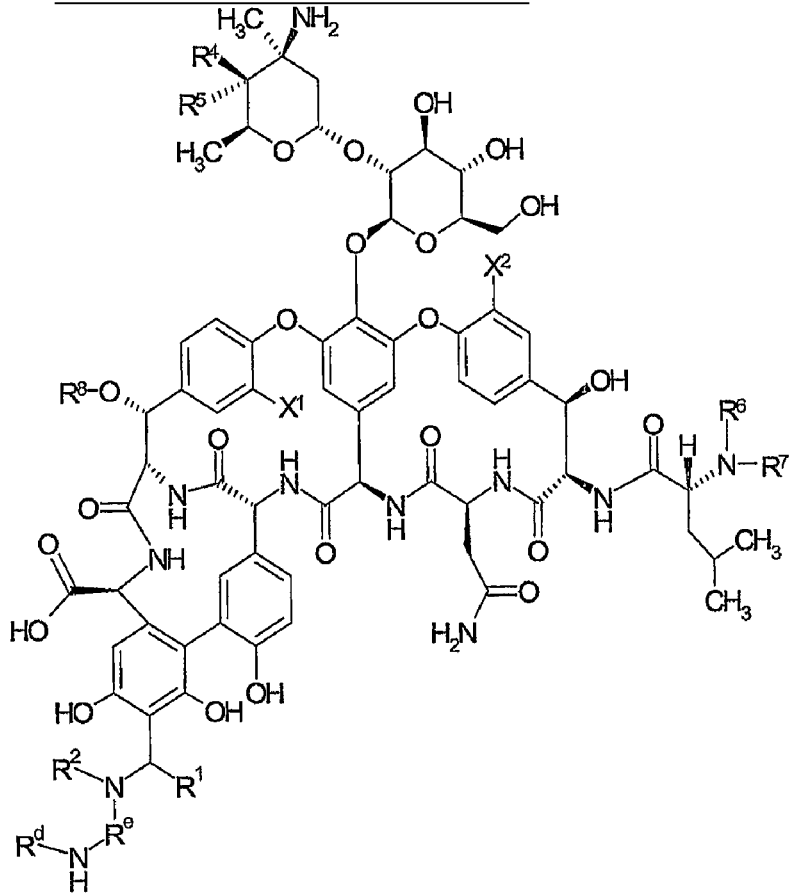

Signed and Sealed this

Seventh Day of August, 2007

JON W. DUDAS  
*Director of the United States Patent and Trademark Office*